United States Patent [19]
Gadsby et al.

[11] Patent Number: 5,341,806
[45] Date of Patent: * Aug. 30, 1994

[54] MULTIPLE ELECTRODE STRIP

[75] Inventors: Peter D. Gadsby, Duvall; David S. Paeth, Seattle; Stephen W. Gross, Snohomish; Thomas D. Lyster, Bothell, all of Wash.

[73] Assignee: Physio-Control Corporation, Redmond, Wash.

[ * ] Notice: The portion of the term of this patent subsequent to Mar. 9, 2010 has been disclaimed.

[21] Appl. No.: 853,006

[22] Filed: Mar. 23, 1992

Related U.S. Application Data

[63] Continuation-in-part of Ser. No. 687,302, Apr. 18, 1991, Pat. No. 5,191,886.

[51] Int. Cl.$^5$ ............................................. A61B 5/0402
[52] U.S. Cl. ..................................................... 128/640
[58] Field of Search ............................ 128/639–641, 128/644, 665, 785, 791–793, 798, 799, 802, 803, 381, 385, 388, 389; 607/115, 139–141, 148, 149, 152, 153

[56] References Cited

U.S. PATENT DOCUMENTS

| | | | |
|---|---|---|---|
| 1,637,829 | 8/1927 | Lurie | 128/802 |
| 3,300,572 | 1/1967 | Dahlgren et al. | 174/69 |
| 3,534,727 | 10/1970 | Roman | 128/644 |
| 3,572,322 | 3/1971 | Wade | 128/640 |
| 3,805,769 | 4/1974 | Sessions | 128/2.06 |
| 4,026,278 | 5/1977 | Ricketts et al. | 128/644 |
| 4,063,352 | 12/1977 | Bevilacqua | 29/630 |
| 4,082,086 | 4/1978 | Page et al. | 128/2.06 |
| 4,121,575 | 10/1978 | Mills et al. | 128/2.06 |
| 4,328,814 | 5/1982 | Arkans | 128/640 |
| 4,334,542 | 6/1982 | Takinishi et al. | 128/642 |
| 4,353,372 | 10/1982 | Ayer | 128/640 |
| 4,365,634 | 12/1982 | Bare et al. | 128/640 |
| 4,393,584 | 7/1983 | Bare et al. | 29/877 |
| 4,398,545 | 8/1983 | Wilson | 128/798 |
| 4,422,461 | 12/1983 | Glumac | 128/798 |
| 4,522,211 | 6/1985 | Bare et al. | 128/640 |
| 4,583,549 | 4/1986 | Manoli | 128/640 |
| 4,633,879 | 1/1987 | Ong | 128/641 |
| 4,635,642 | 1/1987 | Cartmell et al. | 128/639 |
| 4,638,807 | 1/1987 | Ryder | 128/644 |
| 4,669,479 | 6/1987 | Dunseath, Jr. | 128/640 |
| 4,690,148 | 9/1987 | Hess | 128/639 |
| 4,751,928 | 6/1988 | Hallon et al. | 128/644 |
| 4,763,660 | 8/1988 | Kroll et al. | 128/640 |
| 4,798,642 | 1/1989 | Craighead et al. | 156/252 |
| 4,852,572 | 8/1989 | Nakahashi et al. | 128/640 |
| 4,854,323 | 8/1989 | Rubin | 128/644 |
| 4,865,038 | 9/1989 | Rich et al. | 128/665 X |
| 4,865,039 | 9/1989 | Dunseath, Jr. | 128/640 |
| 4,957,109 | 9/1990 | Groeger et al. | 128/640 |
| 5,184,620 | 2/1993 | Cudahy et al. | 128/639 |
| 5,191,886 | 3/1993 | Paeth et al. | 128/640 |

FOREIGN PATENT DOCUMENTS

| | | |
|---|---|---|
| 3347977 | 7/1985 | Fed. Rep. of Germany . |
| 2531-330 | 2/1984 | France . |
| 1158-163 | 5/1985 | U.S.S.R. . |

Primary Examiner—Lee S. Cohen
Attorney, Agent, or Firm—Christensen, O'Connor, Johnson & Kindness

[57] ABSTRACT

Disclosed is an electrode strip (100) for use in electrocardiography comprising a flexible and substantially inextendible substrate (104), a plurality of conductors (114) that extend along the substrate to form a plurality of electrode sites ($V_1$–$V_6$, RA, LA, LL, RL), and a cover layer (122) that insulates the conductors. A plurality of regions of extensibility (102) in the strip allow selective positioning of the electrode sites on a body.

33 Claims, 15 Drawing Sheets

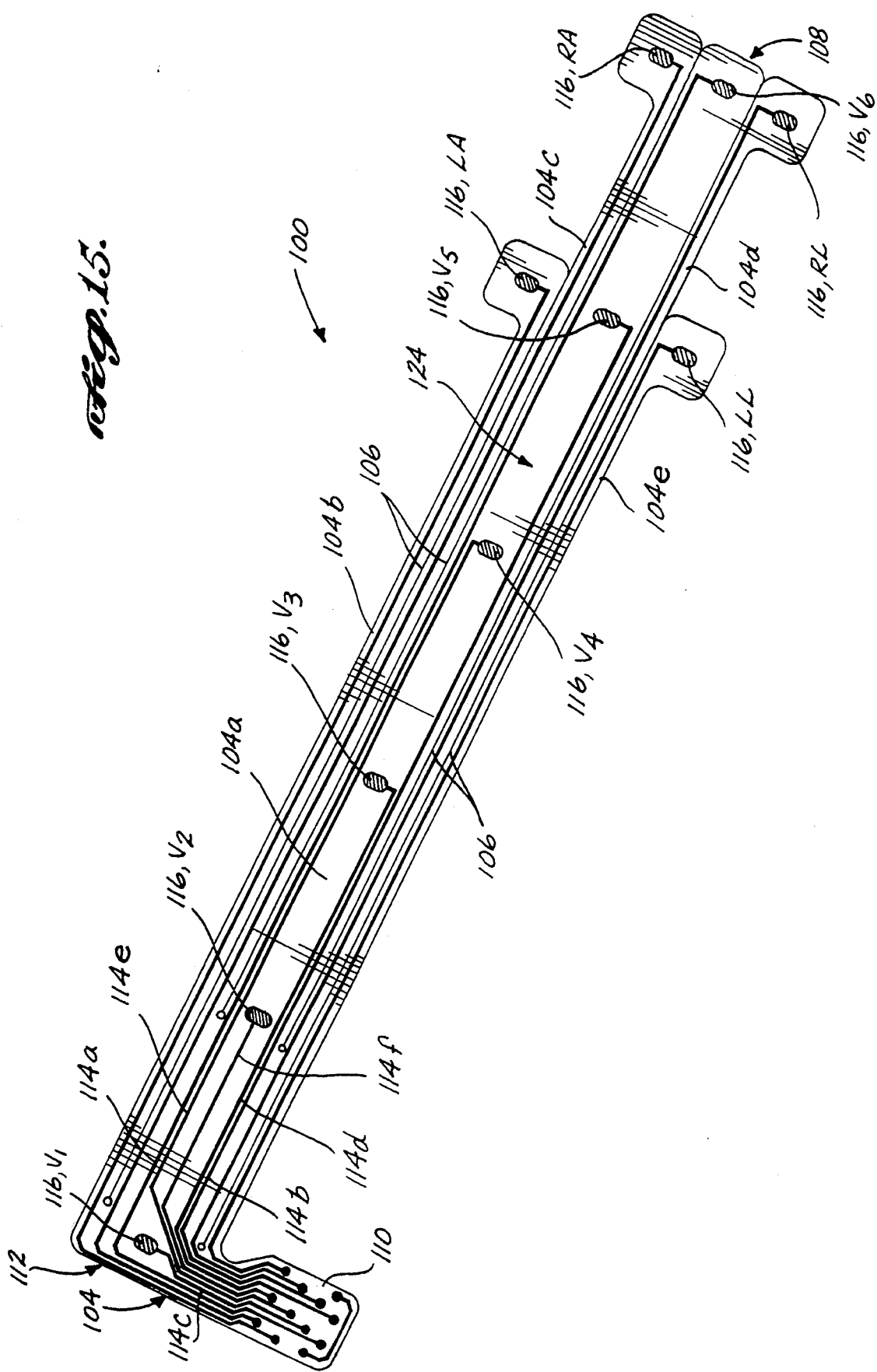

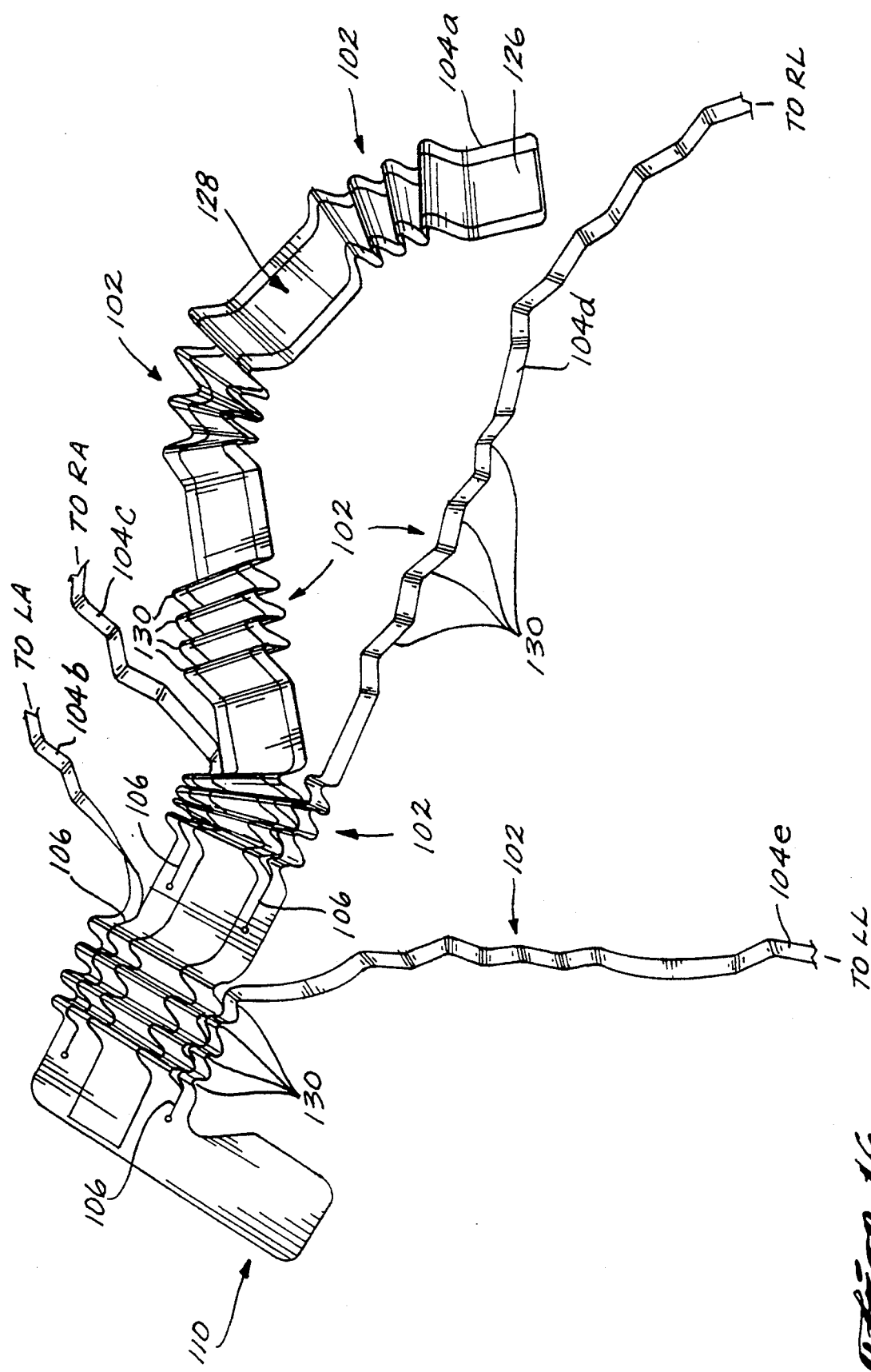

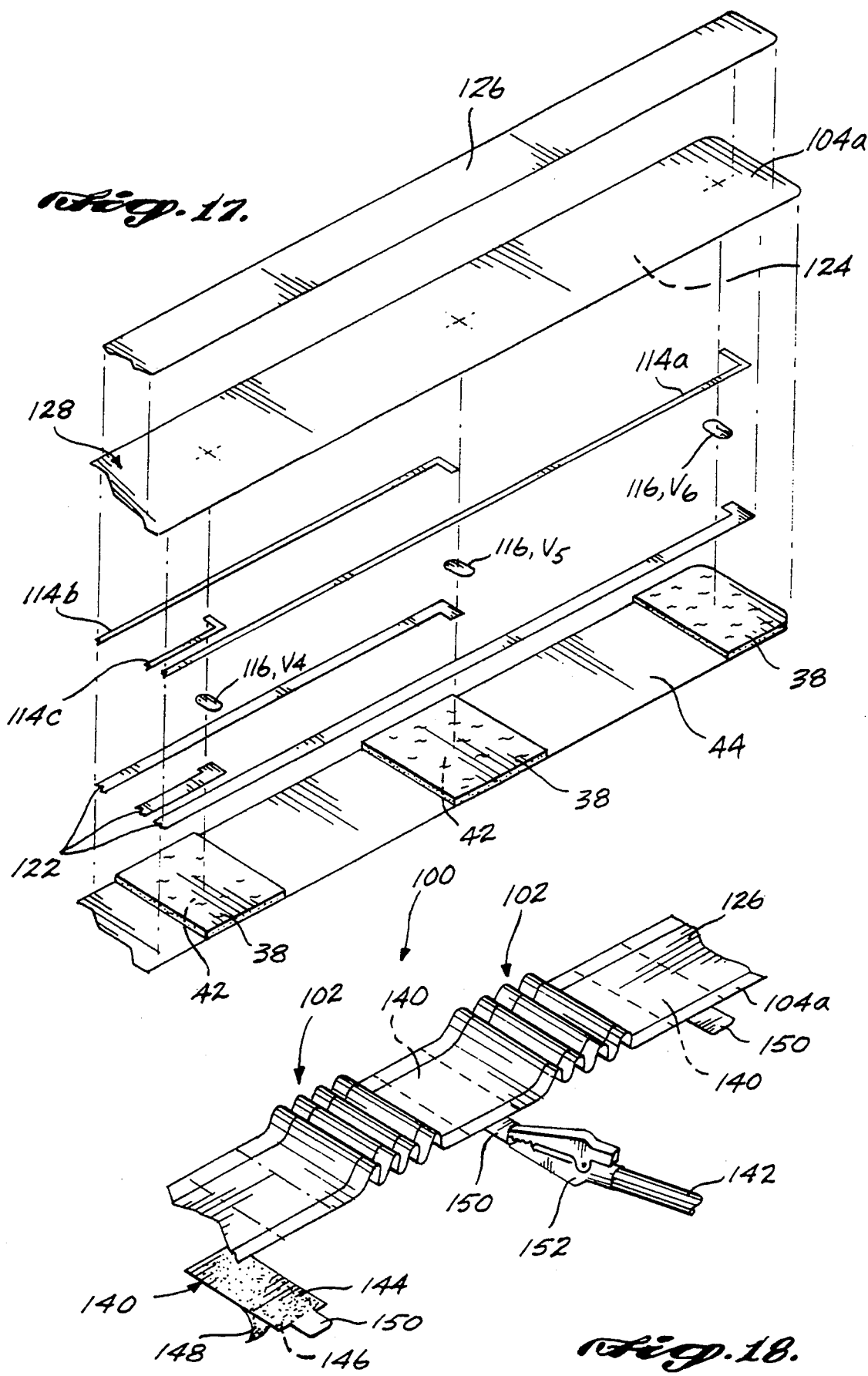

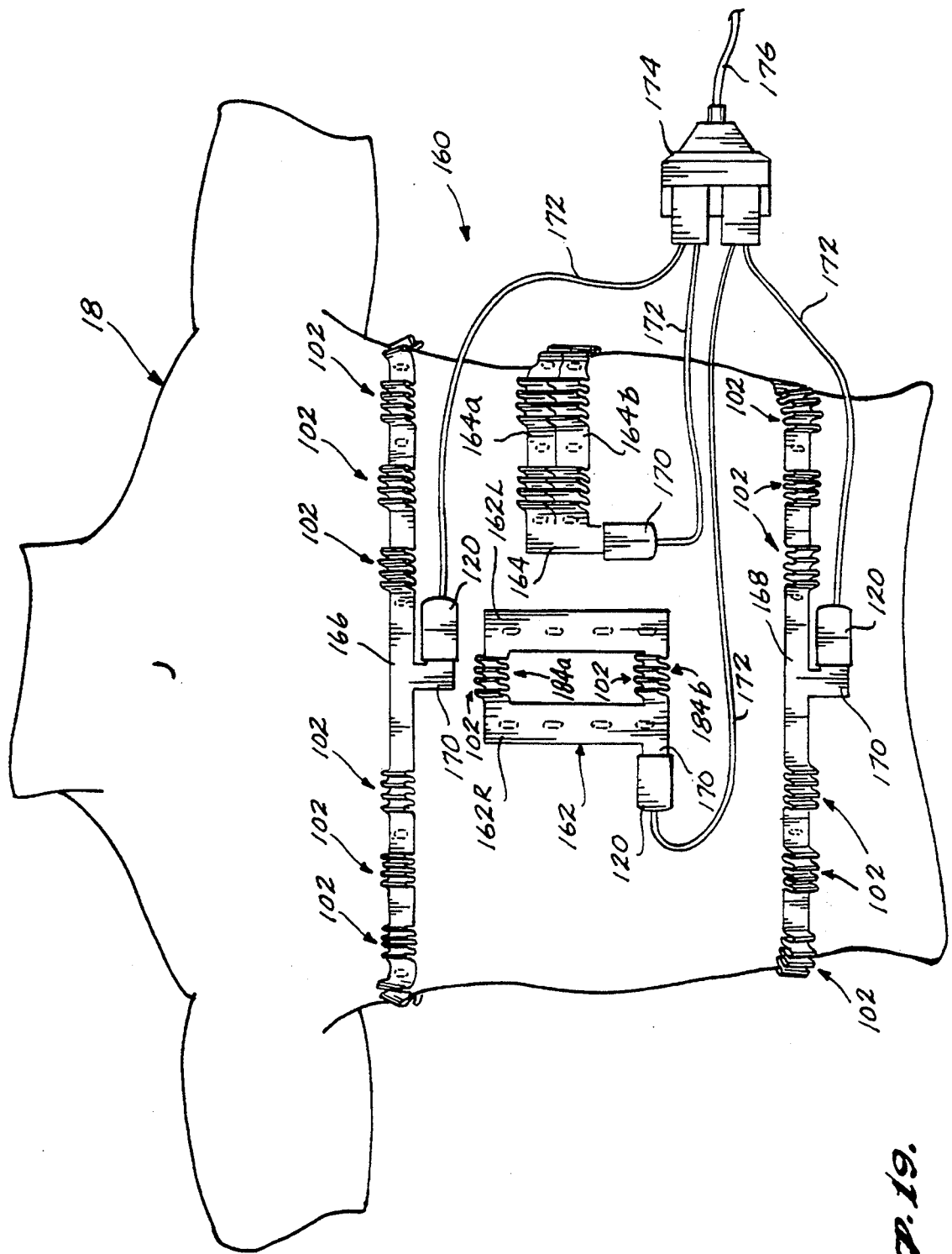

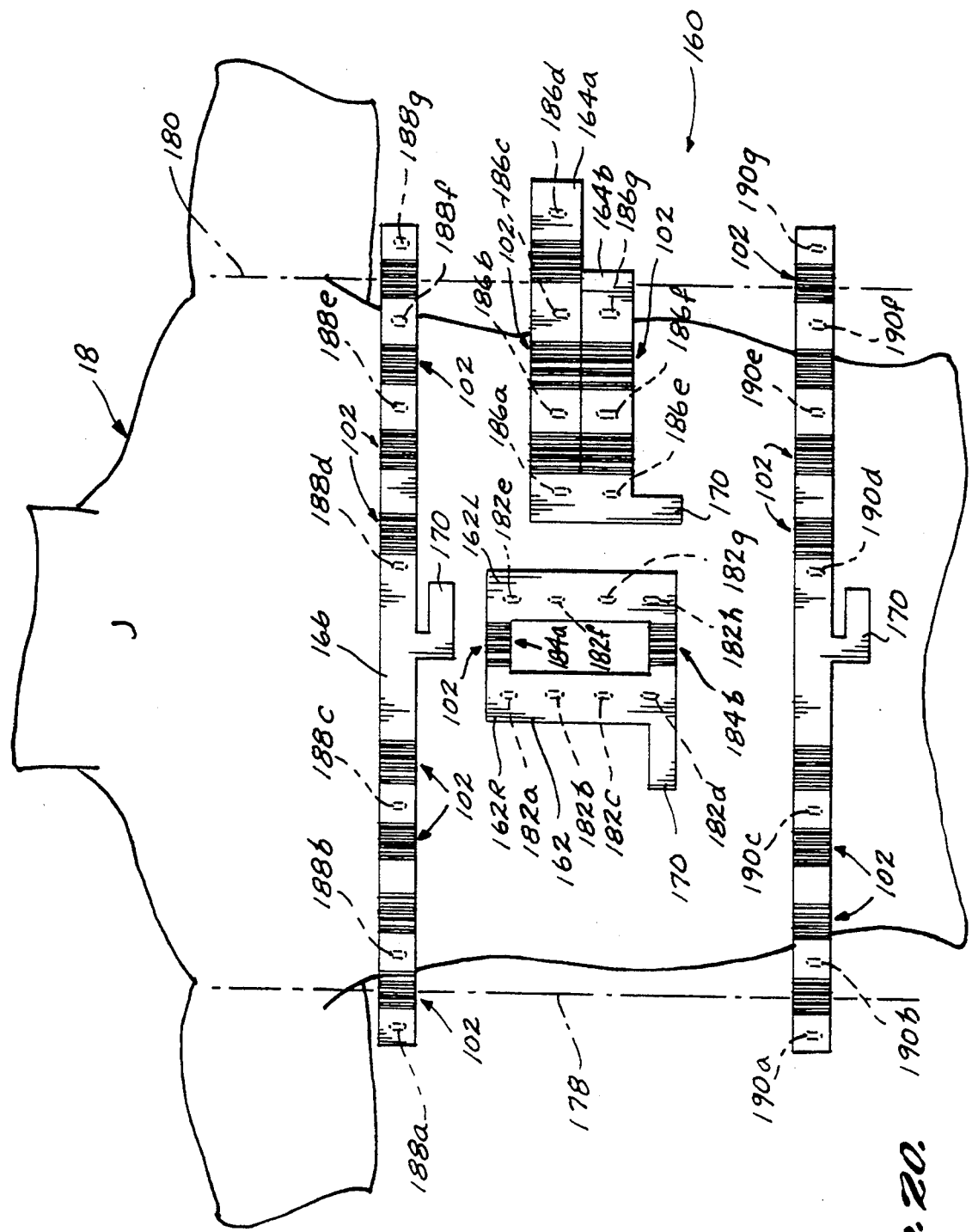

MULTIPLE ELECTRODE STRIP

This application is a continuation-in-part of U.S. patent application Ser. No. 07/687,302, filed Apr. 18, 1991 now U.S. Pat. No. 5,191,886, the benefit of the filing date of which is hereby claimed under 35 U.S.C. § 120. U.S. patent application Ser. No. 07/687,302 is hereby incorporated by reference.

FIELD OF THE INVENTION

The invention relates to monitoring systems and, in particular, to an electrode strip for use in monitoring electrical activities of a living body.

BACKGROUND OF THE INVENTION

Conventional electrocardiography is concerned with the measurement and analysis of voltage potential readings taken from a limited number of anatomically defined locations. The voltages between various locations are combined to form electrocardiograph (ECG) leads that are represented as waveforms and are compared to clinically developed criteria to diagnose or classify the state of a person's heart. One type of conventional electrocardiographic system has focused on the application of ten electrodes to a person's skin; six across the precordial or chest area of the person and one on each of the arms and legs. This type of system is typically called the standard 12-lead ECG system. The electrodes are commonly attached to the body by a conductive gel within an adhesive structure, or by a gel which is both conductive and adhesive.

More recently, electrocardiologists have been experimenting with a body surface potential mapping technique as a tool in scientific investigations and in improving clinical diagnosis of heart disease. In body surface potential mapping, a large number of electrodes are applied to a person's torso to obtain an estimate of the total body surface distribution of cardiac-generated potentials. This distribution is commonly displayed as a series of isopotential contours plotted on a map that represents the person's torso. The resultant isopotential map is then evaluated for the presence of features representing the particular cardiac characteristic of interest.

Proper electrode placement is a major concern in electrocardiography. More particularly, to allow a person's ECG data to be meaningfully compared to clinical data obtained from known populations, the electrode readings must be made at uniformly defined, anatomical locations. Proper placement poses difficulties, in part, because the electrodes must be positioned on people of different sizes. In body surface mapping, the desired electrode sites are arranged in a number of columns and rows, with some mapping systems utilizing as many as 240 body surface electrodes. Thus, proper electrode placement may be further complicated by the large number of electrodes to be attached.

In an attempt to alleviate electrode placement problems, a number of electrocardiograph electrode systems have been developed. One type of system simply uses individual electrodes whose relative positions are unconstrained by the separate and distinct conductive wires that couple the electrodes to a cable that is connected to monitoring equipment. Thus, this system allows individual positioning of the electrodes upon the subject person. A second type of system provides a number of electrodes directly attached to a cable, with differently proportioned electrode-cable sets used with different-sized bodies. Other systems implement a cable or harness whereby individual electrodes attached thereto can be selectively positioned along the cable or harness structure. In one device, the electrodes are connected with spring clips to the harness allowing individual electrodes to be slidingly positioned along the harness.

The electrode arrangements described above are generally cumbersome to use and are often relatively expensive. The time required for proper placement with the more cumbersome prior art systems can be particularly important in emergency situations or when a large number of electrodes are required, for example, to perform body surface mapping. Care must be exercised with a system utilizing a separate lead for each individual electrode so that individual electrodes do not become entangled, a problem that can increase the chance that any given electrode will be placed in the wrong position, particularly in emergency situations. If differently-sized electrode-cable sets are to be used to compensate for differences in body sizes, an electrocardiologist must have electrode-cable sets of several sizes at his or her fingertips. More important, the person charged with placement of electrodes is also required to select the proper size and accurately place the electrodes onto the body in a minimum amount of time. Even then, the electrode-cable set selected may not allow accurate electrode placement on persons between two sizes or at each end of the spectrum of average-sized bodies. Devices utilizing a scheme whereby the individual electrodes can be slidably positioned along an electrode cable or harness are disadvantageous in their bulk and complexity, and again, are not particularly well suited for body surface potential mapping because of the large number of electrodes required.

As can be seen, there is a continuing need to provide an electrode device which allows accurate and timely placement of individual electrodes on the body of a person, whether it be conventional electrocardiography or a technique utilizing body surface potential mapping, while reducing the complexity and cost of the device.

SUMMARY OF THE INVENTION

An electrode strip in accordance with the present invention is a unitary strip for measuring the electrical activities of the heart or other bioelectrical events of a body while still providing a degree of flexibility in the positioning of individual electrodes. A plurality of regions of extensibility in the strip provide adaptive spacing between electrodes. The electrode strip is a potentially disposable alternative to costlier and less manageable cables known in the art. In addition, a number of electrode strips can be configured to be simultaneously and conveniently placed on a patient for use in applications such as body surface potential mapping.

The electrode strip includes a substantially inextendible substrate, a plurality of electrode sites defined on the substrate, and a region of extensibility defined in the substrate between a pair of adjacent electrode sites to allow selective positioning of the adjacent electrode sites on the body. The electrode strip further includes conductive elements for providing an electrical path to each electrode site.

In a preferred embodiment of the invention, the electrode strip includes a layer of malleable material attached to the substrate. The malleable material provides nonelastic extensibility out of the inextendible substrate. The electrode strip includes a plurality of spaced-apart conductors, each one of which extends from the connector area to an individual conductive element at each of the electrode sites. The electrode strip further includes a plurality of dielectric cover layers, a different one of which extends over each conductor.

In one disclosed embodiment of the invention, each region of extensibility is formed by a plurality of transverse folds in the electrode strip to allow adaptive spacing between adjacent apertures. Each fold, in cross section, defines a U-shaped section in the substrate. Other illustrative configurations that can be employed as the regions of extensibility are disclosed.

In currently preferred embodiments of the invention, the conductors are formed on a substrate of polyester resin. Each electrode site is connected to a conductive gel pad which has an adhesive surface to contact a body. A protective release liner is included to protect the adhesive surface of each gel pad prior to attaching the strip to the body.

BRIEF DESCRIPTION OF THE DRAWINGS

The various features and advantages of the invention will be understood in view of the following detailed description taken in conjunction with the following drawings in which:

FIG. 15 is a top elevation view of the electrode strip of FIG. 14 prior to the formation of regions of extensibility between adjacent electrode sites;

FIG. 16 is an elevation view of the electrode strip of FIG. 14;

FIG. 17 is an exploded view of a section of the electrode strip of FIG. 14;

FIG. 18 illustrates an alternative means for connecting the electrode sites of the electrode strip of FIG. 1 or FIG. 14 to monitoring equipment;

FIG. 19 is a perspective view of a body surface potential mapping assembly utilizing a number of electrode strips in accordance with the invention;

FIG. 20 is a schematic view of the body surface potential mapping assembly shown in FIG. 19 and illustrating the placement of the electrode sites along a plane superimposed on a person;

DETAILED DESCRIPTION

Figure 1:
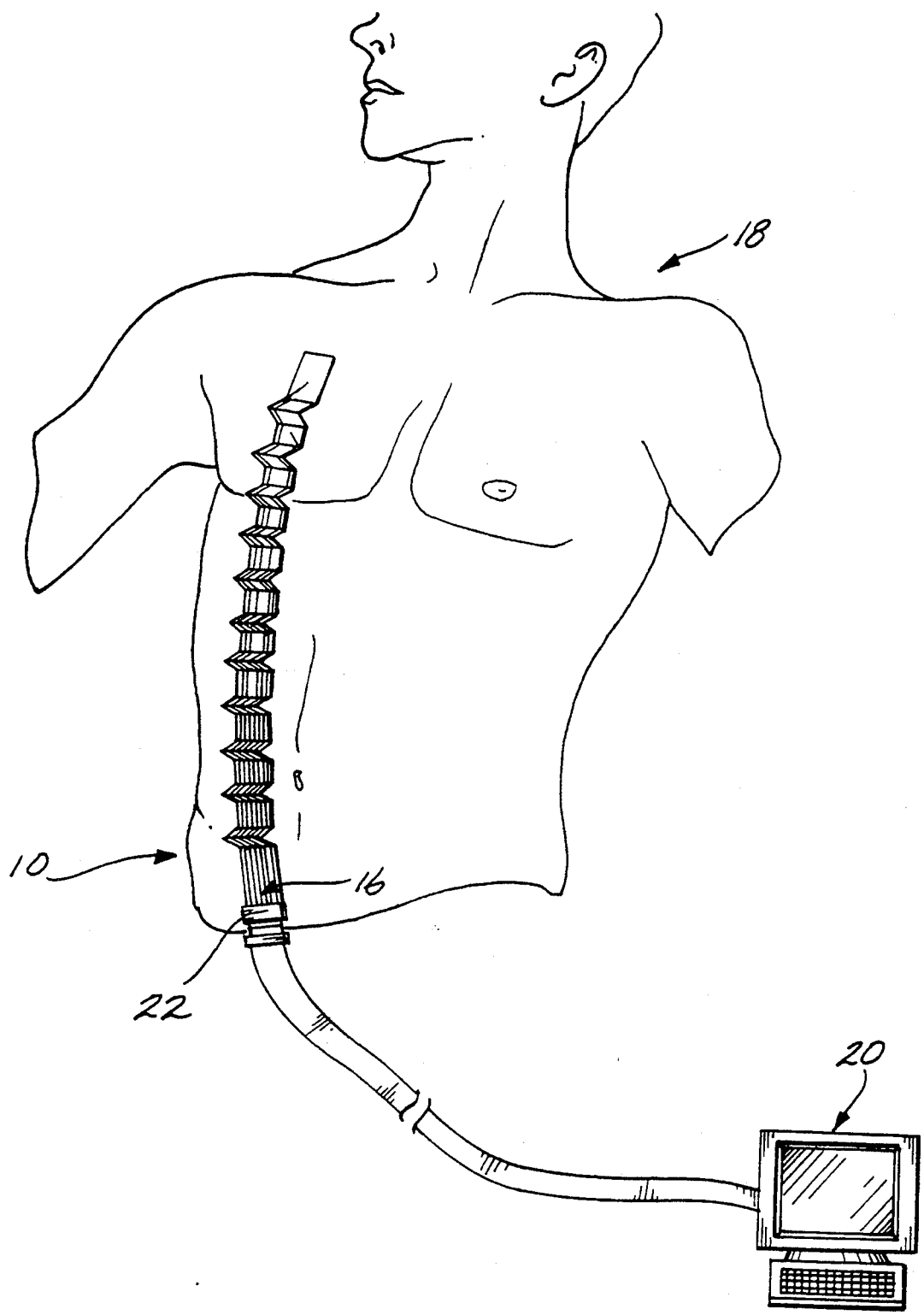
FIG. 1 is a perspective view of a first exemplary embodiment of an electrode strip of the present invention shown in an operative position on the chest area of a person.
Figure 2:
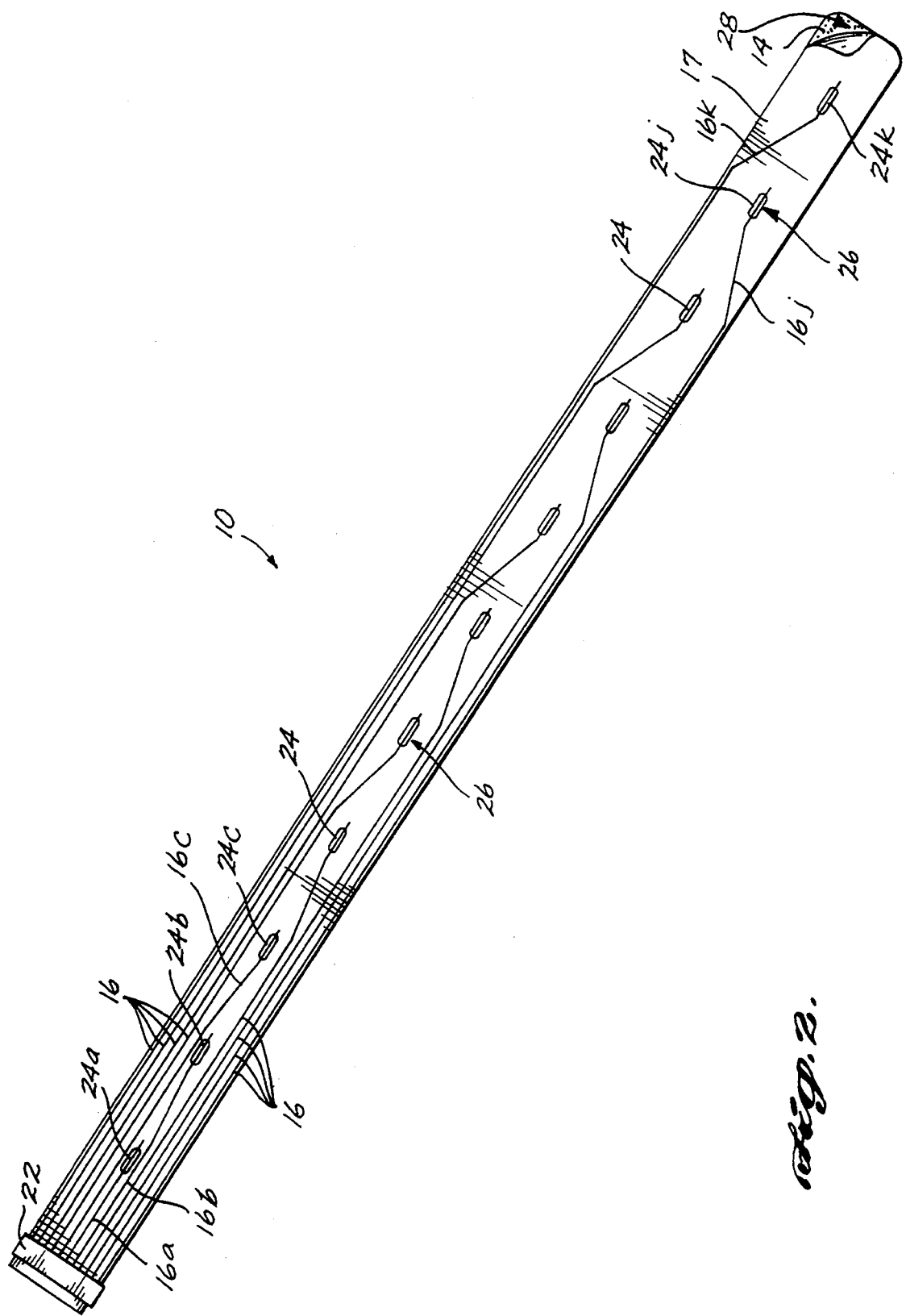
FIG. 2 is a lower, patient-side view of the electrode strip of FIG. 1 prior to the formation of regions of extensibility between adjacent apertures.

In accordance with the present invention, the electrode strip provides a relatively inexpensive and potentially disposable device for measuring the activities of the heart and other muscles and organs of a body while including electrodes which can be selectively positioned to accommodate different-sized bodies. FIGS. 1-2 illustrate a first exemplary embodiment in accordance with the invention. An electrode strip 10 includes an elongate substrate 14, a plurality of spaced-apart conductors 16 that extend along one surface of substrate 14, and an insulating cover layer 17 that insulates all but a portion of each conductor 16. With reference to FIG. 1, the conductors 16 couple electrical signals between a person 18 and various medical and therapeutic equipment, such as a monitoring device 20, which is generally known in the art. As is shown, one end of electrode strip 10 includes a connector 22 which is configured to mate with a cable extending to the monitoring device 20 or other such equipment.

Figure 3:
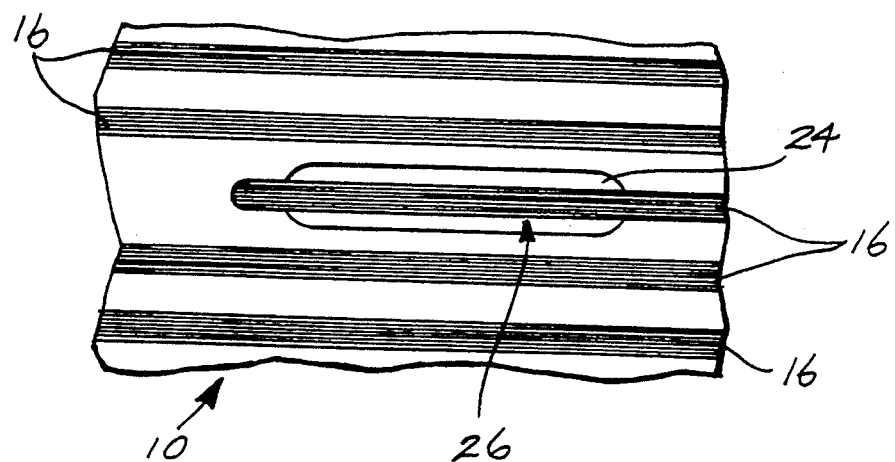
FIG. 3 is an enlarged view of an electrode region (substrate) of the electrode strip shown in FIG. 2.

With reference again to FIG. 2, the cover layer 17 includes a plurality of apertures 24 with each aperture being positioned over a portion of a different one of the conductors 16 to allow electrical contact with the body of a person or other living being. In the arrangement of FIG. 3, the depicted aperture 24 is of elongate oval geometry to form an electrode site 26 of corresponding shape. Various other aperture shapes can be employed as long as the associated conductor 16 passes partially or entirely across the aperture.

The arrangement of conductors 16 as they extend from connector 22 to different ones of the electrode sites 26 may be varied as long as the conductors do not make electrical contact with one another. In the particular embodiment shown in FIG. 2, the conductors are substantially parallel to one another and extend from connector 22 to apertures 24 which are longitudinally spaced apart along the center width of substrate 14. As the conductors 16 approach individual apertures 24, they generally taper toward the center width of the substrate to intersect with the apertures. In that regard, the centermost conductor 16a terminates at the aperture (24a) nearest the connector 22. Conductors 16b and 16c, which lie adjacent the centermost conductor 16a, terminate at the two apertures (24b and 24c) which are second and third nearest the connector 22. The pairing of conductors 16 with apertures 24 continues in the arrangement of FIG. 2, such that the outermost conductors 16j and 16k terminate at the apertures (24j and 24k) furthest from connector 22.

The electrode strip 10 is constructed by depositing or otherwise forming the conductors 16 on a first surface 28 of the substrate 14. In this regard various known processes such as painting, screen printing, vacuum coating or sputtering can be used. The cover layer 17 in which the apertures 24 have been previously cut is then affixed to the first surface 28 of the substrate 14 by means of an adhesive material. As an alternative method of forming the conductors 16, the substrate material may be clad with a layer of conductive material in which the conductors are formed by conventional photolithographic and chemical etching techniques. Preferably, the substrate 14 and cover layer 17 are formed of a polyester resin such as that commercially available under the trade name Mylar ®, each being on the order of 3 mils thick.

Substrate 14, including the conductors 16 and cover layer 17, is flexible but substantially inextensible along its length. A plurality of sections or regions of extensibility 30 are subsequently formed into the substrate between pairs of adjacent electrode sites 26. Illustrative embodiments of the regions of extensibility 30 are shown in FIGS. 4-9B. The formation of materials of the type employed in substrate 14 and cover layer 17 is generally understood by those skilled in their use.

Figure 4:
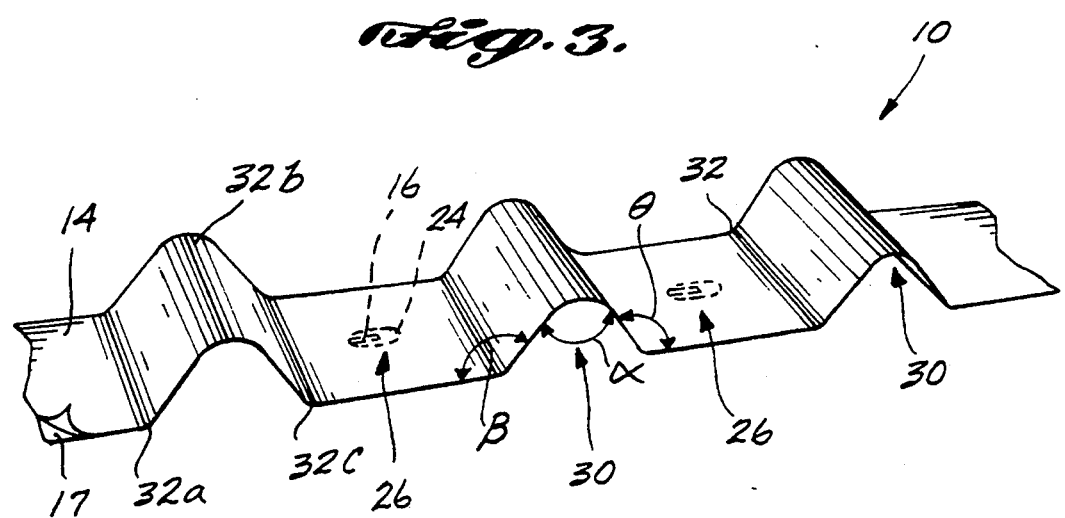
FIG. 4 is a partial perspective view of the electrode strip depicted in FIG. 2 after the electrode strip has been formed to provide regions of extensibility between adjacent apertures.
Figure 5:
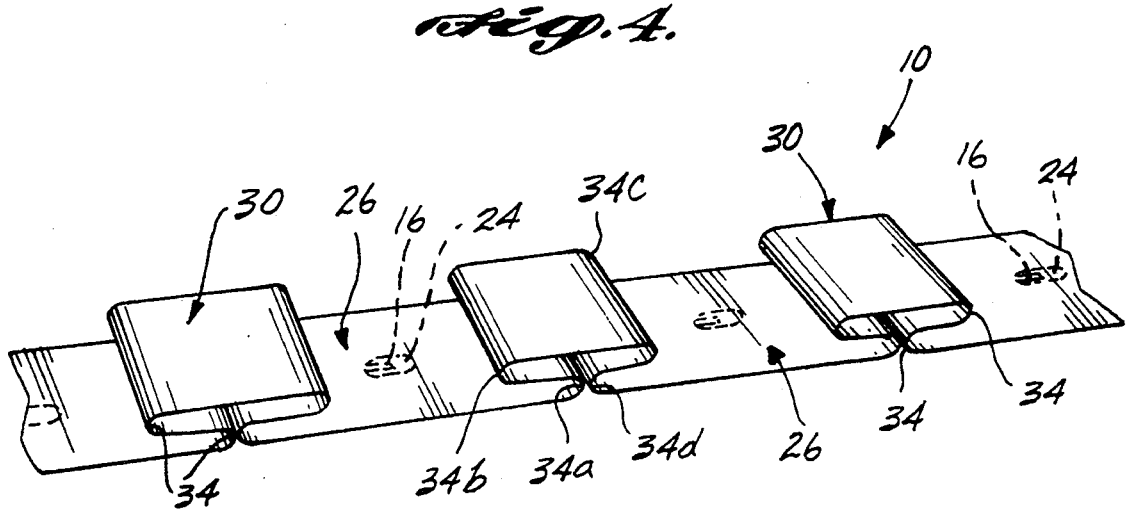
FIG. 5 is a partial perspective view of a second embodiment of an electrode strip of the present invention.
Figure 6:
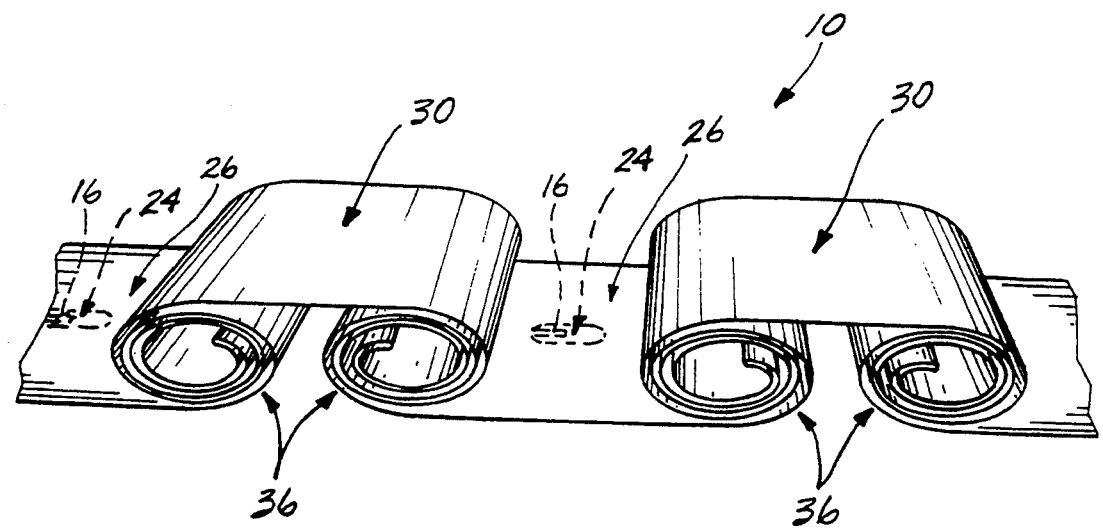
FIG. 6 is a partial perspective view of a third embodiment of an electrode strip of the present invention.

The regions of extensibility 30 as depicted in FIGS. 4-6 are formed into the strip 10 by (1) preshaping the strip using a jig, mandrel or other device; (2) heating the strip while in the preshaped position; and (3) cooling the strip.

An illustrative formation process for the strip 10 involves clamping the strip 10 to a mandrel having a plurality of triangular-shaped sections similar to those illustrated in FIG. 4; immersing the strip in hot water at a temperature between, for example, 180°–212° F.; immersing the strip in cool water, for example, between 45°–60° F.; and, removing the strip from the mandrel. With regard to FIG. 5, each region can be formed by the same process using a jig in place of the mandrel. The jig includes four posts wherein each post causes a 180° turn in the strip 10 when the strip is wrapped around the jig. As can be appreciated, for this process to be used, the substrate 14 (and cover layer 17) must be thermally formable. The optimal parameters of the formation process are dependent upon the particular material used in substrate 14 and cover layer 17.

Figure 7A:
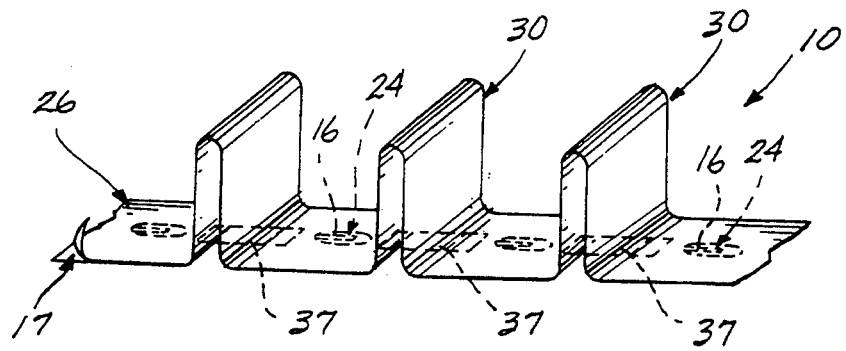
FIG. 7A is a partial perspective view of a fourth embodiment of an electrode strip of the present invention.
Figure 7B:
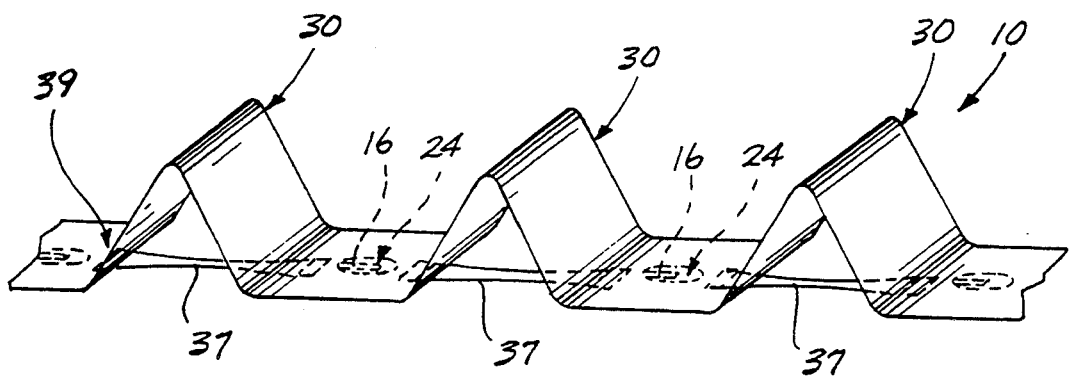
FIG. 7B is a partial perspective view of the electrode strip of FIG. 7A after the regions of extensibility are partially expanded.
Figure 8A:
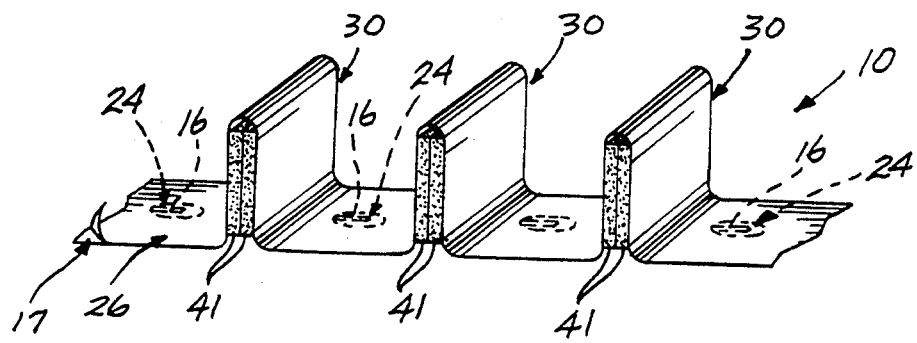
FIG. 8A is a partial perspective view of a fifth embodiment of an electrode strip of the present invention.
Figure 8B:
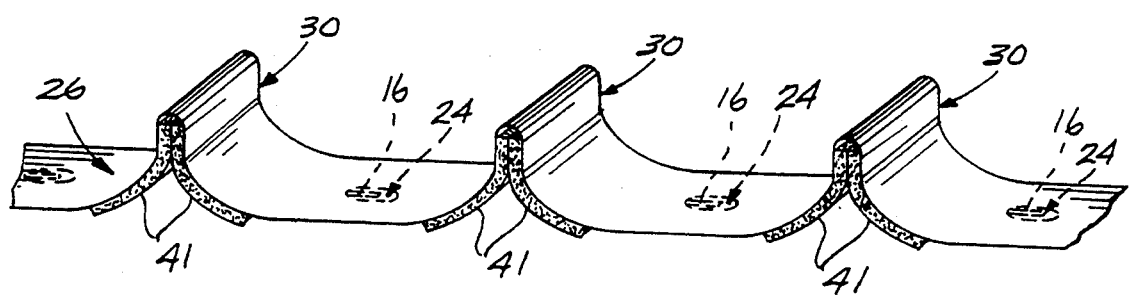
FIG. 8B is a partial perspective view of the electrode strip of FIG. 8A after the regions of extensibility are partially expanded.
Figure 9A:
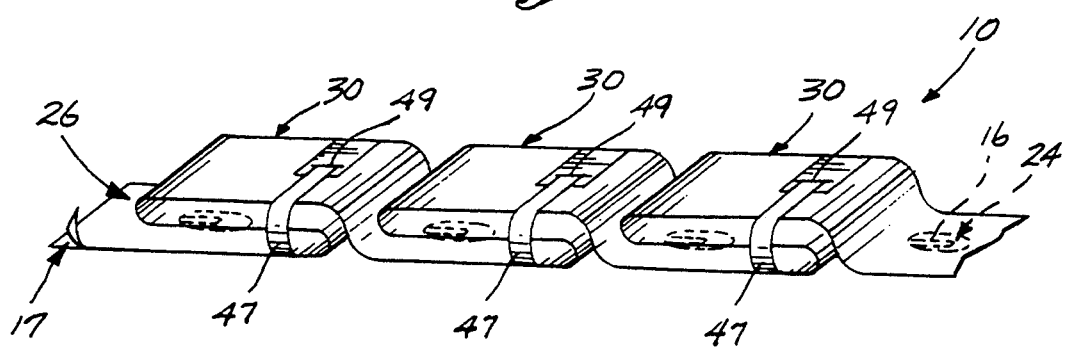
FIG. 9A is a partial perspective view of a sixth embodiment of an electrode strip of the present invention.
Figure 9B:
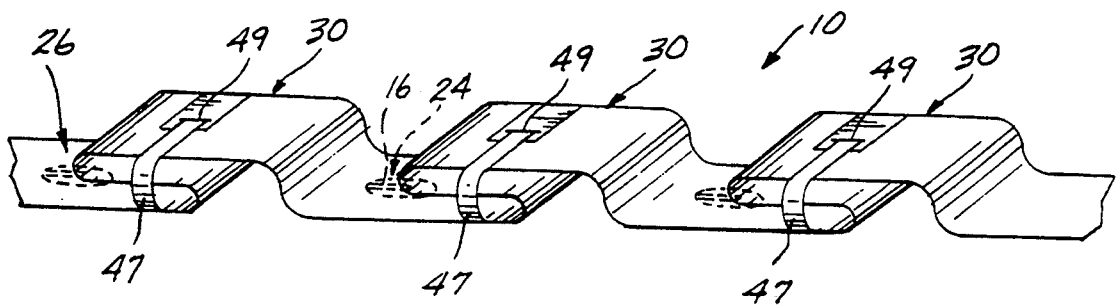
FIG. 9B is a partial perspective view of the electrode strip of FIG. 9A after the regions of extensibility are partially expanded.

The regions of extensibility 30 as depicted in FIGS. 7A–9B demonstrate alternate methods of creating extensible regions. FIGS. 7A, 8A and 9A illustrate alternate regions of extensibility 30 prior to extending the regions to accommodate electrode placement on a body. FIGS. 7B, 8B and 9B illustrate the regions of extensibility 30 in FIGS. 7A, 8A and 9A, respectively, after the regions have been somewhat extended, as if they were positioned on a person.

FIGS. 7A–7B demonstrate the use of a band 37 of material attached to the lower, patient-side surface of the electrode strip 10, between adjacent pairs of the regions of extensibility 30. The bands 37 may be comprised of an elastic material or of an inelastic material that will deform as the regions of extensibility are separated. FIGS. 8A–8B illustrate the use of layers 41 of a material, such as Velcro ®, that separates from itself as the regions of extensibility 30 are separated. In FIGS. 9A–9B, each region of extensibility 30 is formed by doubling a section of the electrode strip 10 over onto itself and holding the section in place using a band 47 of material.

The regions of extensibility 30 as depicted in FIGS. 4–6 are resilient and extendible sections between adjacent electrode sites 26, on the otherwise inextendible substrate 14. The regions of extensibility 30 as depicted in FIGS. 7A–7B can be both resilient and nonresilient extendible sections between adjacent electrode sites 26 on the otherwise inextendible substrate 14. Thus, although the electrode sites 26 are normally separated by predefined distances, the application of longitudinal force to the substrate 14 and regions of extensibility 30 allows the electrode site separation to be altered. As a result, the strip 10 is easily adapted to individual body shapes and sizes while remaining an integral unit.

With reference to FIG. 4, in a first embodiment, each region of extensibility 30 is a tri-fold, triangular-shaped section of substrate 14 formed by three transverse curves or folds 32a, 32b, and 32c. When in the unextended, quiescent state, the geometry of one of the regions 30 roughly parallels that of an isosceles triangle. The angle $\alpha$ of the fold forming the peak of the arc 32b (i.e., the angle opposite the base of the isosceles triangle) is less than 60° with the angles $\beta$ and $\theta$ of the adjacent folds (32a and 32c) being less than 120° each. The angle $\alpha$ of fold 32b will increase (i.e., approach or exceed 60°) when the electrode strip is in effect stretched to increase the distance between adjacent electrode sites 26; conversely, the angle $\alpha$ will decrease to less than 60° when the adjacent electrode sites 26 are moved toward one another. The angles of each fold 32 described offer a desirable degree of extendibility for each region of extensibility 30.

With reference to FIG. 5, in a second embodiment, each region of extensibility 30 includes four transverse folds 34 which collectively form a stubby T-shaped section of substrate 14. More particularly, each fold 34 represents a 180° turn in the substrate. The first fold 34a and fourth fold 34d collectively form the vertical portion of the T, respectively. The folds 34b and 34c form the horizontal portion of the T.

With reference to FIG. 6, in a third embodiment, each region of extensibility 30 includes two opposing spiral wound regions 36. Each spiral wound region 36 is formed by doubling a section of substrate 14 over onto itself and coiling the doubled-over region into a spiral having at least a half turn. In the embodiment of FIG. 6, the spirals forming each region of extensibility have on the order of two and one-half turns. The spiral wound regions 36 of a particular region of extensibility 30 will tend to unwind as the electrode strip 10 is in effect stretched to increase the distance between adjacent electrode sites 26.

With reference to FIGS. 7A and 7B, in a fourth embodiment, each region of extensibility 30 includes a fold in the electrode strip 10 that is maintained by a band 37 of material. Lateral force applied to the electrode strip 10 causes the band 37 to stretch between the electrode sites 26. The bands 37 are attached to the electrode strip by, for example, applying an adhesive, or using heat to bond the materials together. Band 37 stretches resiliently if a material such as natural rubber is used or inelastically if a thin plastic sheet of polyethylene is used. The bands 37 are preferably attached to the lower, patient-side surface of the electrode strip 10 as depicted. Alternatively, a pair of bands may be coupled to the sides of each fold.

With reference to FIGS. 8A and 8B, in a fifth embodiment, each region of extensibility 30 includes a fold in the electrode strip 10 that is maintained by layers of material 41. Layers 41 are peeled apart when lateral force is applied to electrode strip 10, as depicted in FIG. 8B. Suitable materials for use as the layers 41 include Velcro ®, an adhesive with poor self-stick properties, a nonadhesive material with cohesive properties, or a fragile material which tears apart when lateral force is applied to the strip. The layers are preferably adhesively attached to the electrode strip 10.

With reference to FIGS. 9A and 9B, in a sixth embodiment, each region of extensibility 30 is a section of the electrode strip that is doubled over onto itself and held in place by a band 47. The band 47 is constructed from a part of the substrate 14 itself, or may be a separate strip of material that is looped around the electrode strip. In FIGS. 9A and 9B, each band comprises two strips of the substrate 14 that are coupled together by extending one of the strips through a slot 49 in the other strip. As an alternative, the two strips may be coupled together by an adhesive bond.

The degree of adjustment that can be made to the spacing between adjacent electrode sites 26 is dependent, first upon the distance between adjacent apertures 24, and second by the shape, size, and complexity of the regions of extensibility 30. In general, these factors can be varied during both the manufacturing and forming processes of the strip 10 to tailor the strip to any desired application. For example, the embodiment of FIG. 6 may be useful in some situations because the relatively large amount of substrate 14 within each spiral wound region 36 allows a great deal of latitude (in separation) when positioning the electrode sites 26 on a body.

The strip 10 can also be tailored by selecting the number of electrode sites to accommodate specific needs. As another example, a precordial strip requires six electrode sites. To allow strip 10 to properly adjust to the general population in a precordial application, the regions of extensibility 30 are configured to provide a longitudinal adjustment on the order of several centimeters between adjacent electrode sites 26. Further, the nonlinear nature of the anatomically defined electrode locations for precordial monitoring requires that the regions of extensibility 30 be formed to allow both longitudinal and curvilinear adjustment of the electrode strip 10. A strip could be constructed in accordance with the invention to meet these constraints by, for example, employing multiple folds which when bent will conform in a curvilinear fashion similar to the spreading of a fan.

Figure 10:
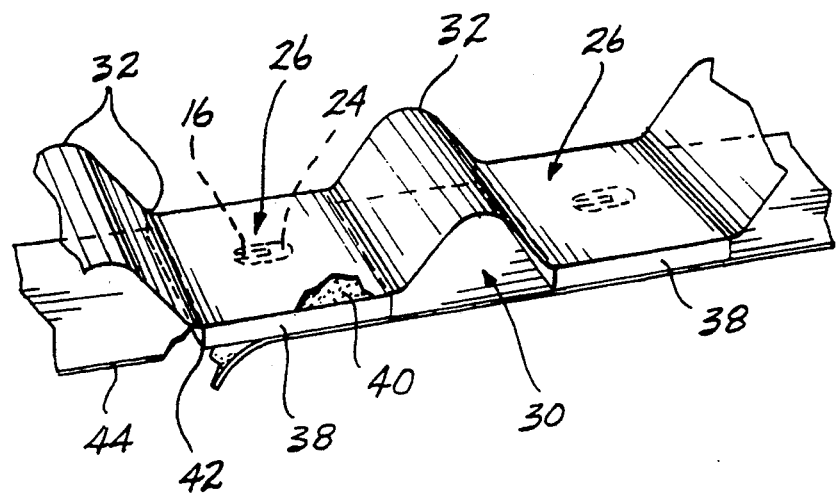
FIG. 10 is a partial perspective view of the electrode strip of FIG. 1 illustrating the use of an adhesive conductive gel pad to interface the electrode strip with the body of a person.

With reference to FIG. 10, the conductors 16 must be electrically coupled to the body of a person or other being (i.e., in signal communication with the body). One method of establishing this electrical contact is through a plurality of conductive gel pads 38 associated with the various electrode sites 26. Thus, the electrode sites 26 do not directly contact the skin. Rather, the conductors 16 terminating at each electrode site 26 are coupled to the skin via the gel pads 38. Each pad has adhesive properties on both oppositely disposed surfaces—an upper surface 40 to attach the gel pad 38 to the strip 10 and a lower surface 42 to detachably mount the pad to the body of a person (not shown). Adhesive, ionically conductive gels in this form are generally known in the art.

Once mounted to a person, the entire lower surface 42 of the gel pads 38 will provide ionic conductivity between the person's skin and the conductors 16. The impedance of the electrode/patient interface is determined primarily by the area of the lower surface 42 and not the size of the electrode site 26. This property allows the apertures 24 and the conductors 16 to have a relatively small size without affecting the strength of the signals monitored by the end equipment, for example, the monitoring device 20 shown in FIG. 1.

A desirable skin surface area to obtain electrode readings is on the order of one square inch (i.e., 6.45 square centimeters). Preferably, the strip 10 is provided with one-inch-square gel pads 38 which are preattached to the area surrounding each electrode site 26. An outer liner 44 protecting the adhesive on the lower surface 42 of the pads 38 can then be removed just prior to attaching the strip to the body. In one embodiment, shown in FIG. 10, the protective outer liner 44 is a single strip which covers the lower surfaces 42 of all of the gel pads 38. In this embodiment, removal of the single liner 44 will expose the lower surface 42 of each gel pad 38 for placement on the body.

Figure 11:
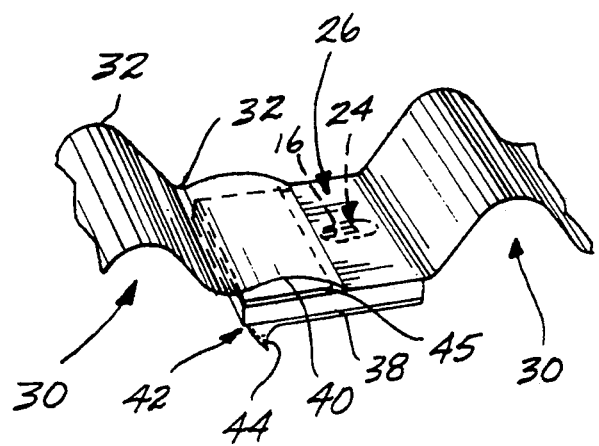
FIG. 11 is a partial perspective view of the electrode strip of FIG. 10 where the ends of each pad opposite the electrode contact with the strip are allowed to remain free of attachment to the strip.

With reference to FIG. 11, a second method of attaching the gel pads 38 to the electrode strip 10 is illustrated. When applied to a person's body (not shown), longitudinal extension of the strip 10 tends to cause the regions of the substrate 14 around the electrode sites 26 to bend away from the body, i.e., presenting a concave surface to the person's body. To accommodate such bending while maintaining electrical contact between the body and the electrode sites 26, only a portion of the conductive gel pad 38 is attached to the electrode site 26. More specifically, one end of the upper surface 40 of the gel pad 38 is adhesively attached to the substrate 14 at the aperture 24. The remaining portion of the upper surface 40 of gel pad 38, adjacent the electrode site 26, includes a strip 45 of paper or other suitable material that prevents it from adhering to the electrode strip. The entire lower surface 42 of the gel pad 38 is still attached to the person's body. When the gel pad 38 is adhesively joined to the person's body it effectively couples electrical signals to and from the body while still allowing the electrode site 26 to bend away from the body. As previously noted, the protective outer liner 44 applied to the adhesive regions on the lower surface 42 must be removed prior to attaching the pad 38. Where adhesion of the pads 38 to sites 26 is limited by the strips 45, it will be noted that removal of the outer liner 44 must proceed starting from the end of strip 10 that is opposite the limited adhesion end of pads 38.

Figure 12:
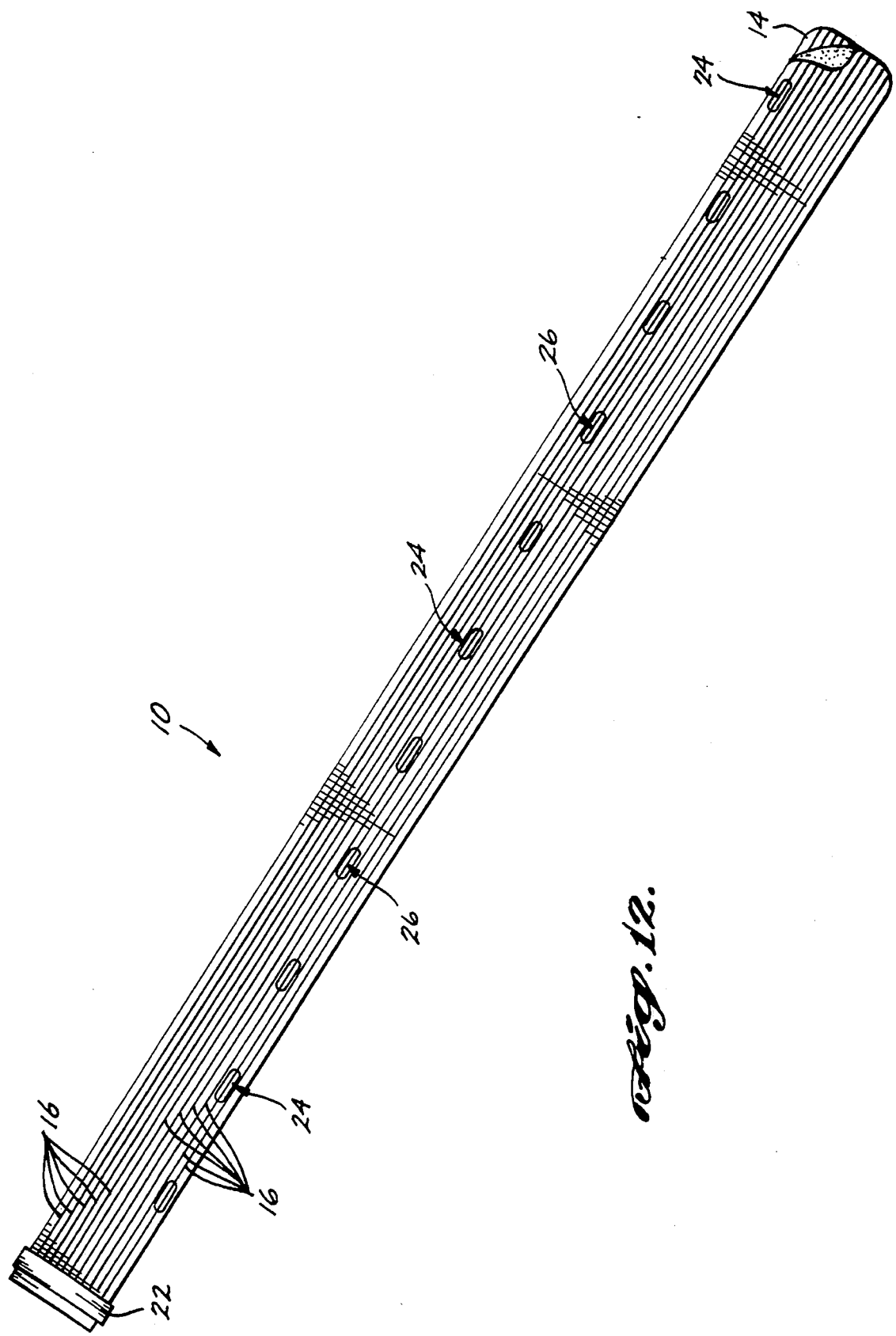
FIG. 12 is a patient side view of an electrode strip substrate which includes an alternative pattern of apertures, and hence, electrodes.

As is discussed above, the arrangement of the conductors 16 as they extend to the apertures 24 is not of critical importance. With reference to FIG. 12, in an alternative arrangement, each conductor 16 extends substantially the entire length of the substrate 14, rather than having the individual conductors terminate after reaching an aperture as in FIG. 2. In this arrangement, the conductors 16 are substantially parallel to one another and to the length of the strip 10. The conductors 16 are equally spaced apart across the width of the strip. The corresponding apertures 24 associated with the conductors 16 are located at varying widths along the strip 10 and thus are not in longitudinal alignment with the strip as are the apertures of FIG. 2. However, it should be noted that this arrangement of apertures 24, and hence electrode sites 26, will not cause electrode placement problems with respect to the person's skin because the gel pads 38 are longitudinally aligned with the strip 10 and it is the gel pads and not the actual electrode sites 26, which contact the skin (as described above).

The alternative arrangement of conductors and apertures in FIG. 12 allows the substrate 14 and conductors 16 to be manufactured in a continuous process with adjustments of the apertures' locations in the cover layer facilitating particular applications of the strip. For example, some applications may require the apertures to be spaced further apart or, conversely, closer to one another. This is accomplished with the arrangement of FIG. 12 simply by adjusting the longitudinal spacing between the apertures. In contrast, the embodiment shown in FIG. 2 may require an adjustment in lead layout, as well as aperture positions, to alter the substrate 14 for different applications.

Figure 13:
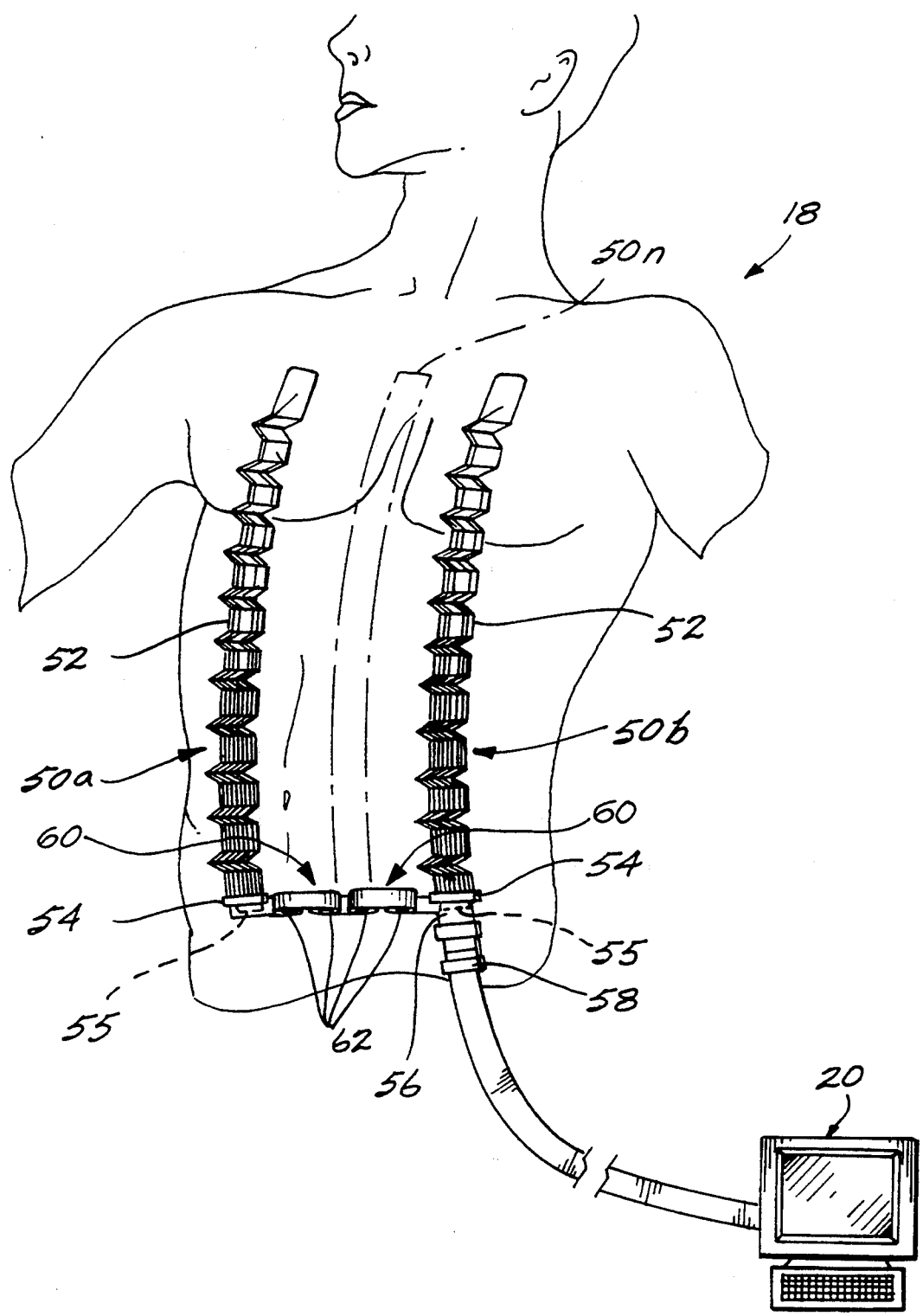
FIG. 13 is a perspective view of a number of the electrode strips of FIG. 1 shown in an operative position on the chest area of a person.

Body surface potential mapping techniques often require the placement of a large number of electrodes on a person in an arrangement comprising any number of columns and rows. With reference to FIG. 13, an exemplary arrangement including a number of columns of electrodes is shown. Each column includes an electrode strip. In that regard, a first electrode strip 50a is illustrated on the right side of the person 18 and a second electrode strip 50b is illustrated on the person's left side. An electrode strip 50n (shown in phantom) representing the nth strip attached to the person is also illustrated. The electrode strips 50 are substantially similar to the electrode strip 10 of FIG. 1. In that regard, each electrode strip 50 includes a plurality of spaced-apart conductors 52 and a connector 54 at one end thereof.

The electrode strips 50 are joined through their connectors 54 to a plurality of connectors 55 in a connector strip 56. The connectors 54 of the electrode strips 50 cooperatively interact with the connectors 55 of the connector strip 56 to couple electrical signals therebetween. Further, the connector strip 56 includes a plurality of spaced-apart conductors (not shown) which couple electrical signals between the conductors 52 (and, hence, the person 18) and the monitoring device 20. As is shown, the connector strip 56 includes a cable connector 58, which is configured to mate with a cable extending to the monitoring device 20 or other such equipment.

The connector strip 56 utilizes the technology of the present invention to allow flexibility in the placement of the electrode strips 50. To this end, the connector strip 56 includes a number of extensible regions 60 similar to the regions of extensibility 30 of the electrode strip 10. Preferably, the extensible regions 60 each include two opposing spiral wound regions 62 similar to the spiral wound regions 36 of FIG. 6. As will be appreciated by those skilled in the art, the number of strips so depicted in FIG. 13 can be increased to provide a larger number of readings. Further, the length, width and shape of the connector strip 56 can be adjusted to accommodate the number and arrangement of strips employed.

Figure 14:
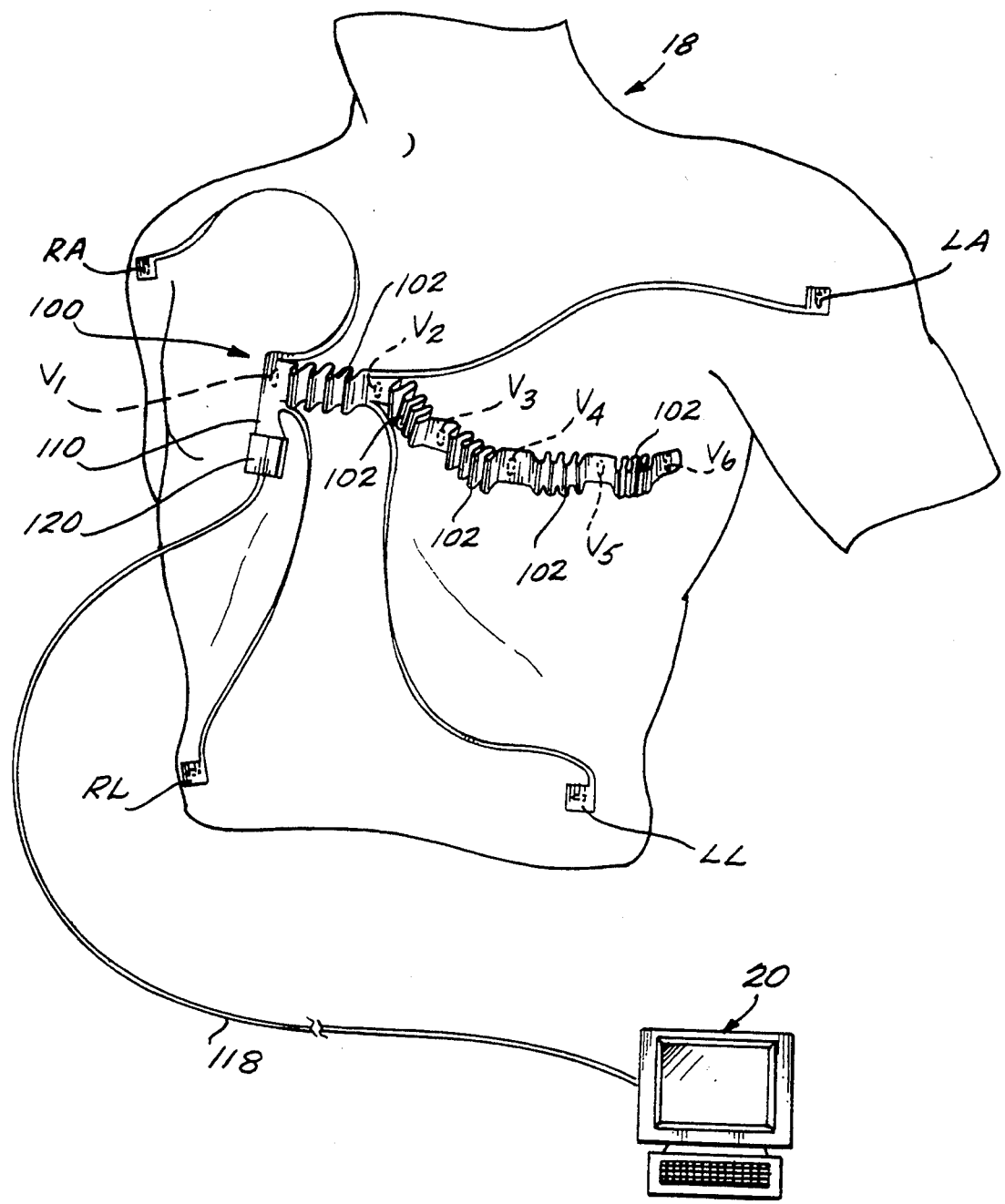
FIG. 14 is a perspective view of a second exemplary embodiment of an electrode strip of the present invention shown in an operative position on a person, with electrodes located at a plurality of precordial and limb sites.

FIGS. 14–16 illustrate a second exemplary electrode strip 100 constructed in accordance with the invention. Electrode strip 100 is tailored for use with a standard 12-lead ECG system, wherein six electrodes are placed across the chest of a person at precordial placement positions $V_1$–$V_6$ and four electrodes are placed on the arms and legs (or torso) at right arm RA, left arm LA, left leg LL, and right leg RL placement positions. As is shown most clearly in FIG. 16, the electrode strip includes a plurality of regions of extensibility 102 that allow selective and adjustable spacing of the electrodes on the body of a person 18. In contrast to the regions of extensibility 30 of electrode strip 10 (shown in FIG. 1), the regions of extensibility 102 are better suited to provide curvilinear bending, as well as longitudinal extension and contraction of the strip. Thus, the required curvature of strip 100 between the precordial placement positions is readily achieved.

A top, elevation view of the electrode strip 100, prior to formation of the regions of extensibility 102, is illustrated in FIG. 15. The electrode strip 100 includes a substantially elongate substrate 104 that is separable into five substantially elongate sections 104a–104e along cut-lines 106. It is assumed in FIG. 15 that the substrate 104 is transparent to allow the conductors and electrode sites on the lower, patient-side of the strip to be clearly shown. The entire substrate 104 may be formed of a single material and then cut along the cut-lines 106. In a preferred use, the cut-lines 106 are only perforated and the electrode strip 100 is packaged and sent to the end-user as a single, elongate piece, with each substrate section 104a–104e including the regions of extensibility 102 (not shown in FIG. 15). During placement of the device, the substrate sections 104b–104e are then partially separated from each other at a first end 108 along the perforated cut-lines 106 and stretched to contact the limb placement positions RA, LA, LL and RL, respectively.

In a preferred configuration, the substrate 104 includes an end segment 110 that extends perpendicularly from a second end 112 of the electrode strip. A plurality of spaced-apart conductors 114 begin at the end segment 110, extend along the lower (patient-side) surface of the substrate 104, and terminate at spaced-apart locations along the electrode strip. Each conductor includes a circular-shaped area at the end segment 110, providing a sufficient surface area to allow contact by a connector clamp, described below. Opposite the connector end, i.e., at the terminating end, each conductor includes an elongate oval-shaped area of conductive material. Preferably, a second elongate oval-shaped layer 116 of conductive material is placed in electrical contact with the terminating end of each conductor 114 to form electrode sites, i.e., precordial sites ($V_1$–$V_6$) and limb sites (RA, LA, LL and RL). Each oval-shaped layer 116 is then coupled to the person's skin, preferably through a conductive interface such as the gel pads 38, depicted and described in reference to FIGS. 10 and 11. The conductors 114, including the circular-shaped beginning end and oval-shaped terminating end, are preferably formed of silver ink tracings. Excluding the ends, a suitable width for the conductors is a width on the order of 60 mils (1.5 mm).

With reference again to FIG. 14, the conductors (not shown) couple electrical signals between the person 18 and medical and therapeutic equipment, for example, monitoring device 20 via a cable 118. The cable 118 includes at least ten conductive leads to couple each of the conductors of the electrode strip to the monitoring device 20. The cable 118 is releasably coupled to the electrode strip by a spring-loaded clamp 120 that is configured to mate with the end segment 110 of the strip. In one embodiment, the clamp includes at least ten conductive teeth, one for each conductor, with each tooth being coupled to a different one of the conductive leads in cable 118. When coupled to the end segment 110, the teeth engage their respective conductors in the circular-shaped area of each conductor (shown in FIG. 15) and are held against the conductors by the spring housed within the clamp. The clamp 120 is described and illustrated in greater detail in FIGS. 21 and 22 and accompanying text.

The particular arrangement of conductors 114, as they extend from end segment 110 to the precordial and limb electrode sites, is not of substantial importance as long as the conductors remain insulated from one another. In the particular embodiment shown in FIG. 15, the conductors generally extend in a parallel fashion from the end segment toward the electrode sites.

The conductors on substrate section 104a extend from the end segment 110 along the substrate until reaching individual precordial electrode sites $V_1$-$V_6$. In that regard, the outermost conductors 114a and 114b (on substrate section 104a) extend to sites $V_6$ and $V_5$, respectively. The conductors 114c and 114d, adjacent the outermost conductors, extend to sites $V_1$ and $V_3$, respectively. The innermost conductors, 114e and 114f, extend to sites $V_4$ and $V_2$, respectively.

The conductors on substrate sections 104b–104e extend from the end segment 110 to the limb sites RA, LA, LL and RL, respectively. The substrate sections are relatively narrow as they extend from the end segment 110 to each limb site. At each limb site, however, the associated substrate section becomes wider and has a substantially square-shaped segment to accommodate the limb sites, i.e., including the oval-shaped layers 116. As the conductors extend from the end segment and reach the square-shaped segments, they form a right-angle out and away from the center of substrate 104a to intersect the limb sites RA, LA, LL and RL.

Each of the conductors 114 is insulated from the person by a separate dielectric cover layer 122. The cover layers 122 are preferably formed of a UV curable dielectric coating such as those manufactured by Acheson Colloids Company. The cover layers 122 are preferably deposited onto the electrode strip through a single silk screening process whereby only those areas needing insulation are covered. This method of dielectric placement is advantageous as it conserves dielectric material. As will be appreciated, the entire lower patient-side surface of the electrode strip, with the exception of the electrode sites and the end of each conductor, may be covered with a single dielectric layer if desired.

An exploded, sectional view of the first end 108 of the substrate 104a is shown in FIG. 17, including the conductors 114, oval-shaped layers 116 and cover layers 122. Only three of the cover layers 122 are shown in FIG. 17. The cover layers are slightly wider than the conductors they insulate and extend from the end segment 110 to the oval-shaped layers 116. For example, if the conductors are 60 mils (1.5 mm) wide, the cover layers 122 are preferably on the order of 100 mils (2.5 mm) wide. As will be appreciated, the conductors may alternatively be insulated by a continuous layer of dielectric having a plurality of apertures extending orthogonally therethrough, and spaced along the dielectric at locations corresponding to the oval-shaped layers 116, in a manner similar to electrode strip 10 of FIG. 1.

The electrode strip 100 is constructed by depositing or otherwise forming the conductors 114 on a lower (patient-side) surface 124 of the substrate 104. In this regard, various known processes such as painting, screen printing, vacuum coating or sputtering can be used. As an alternative method of forming the conductors 114, the substrate may be clad with a layer of conductive material in which the conductors are formed by conventional photolithographic and chemical etching techniques. The cover layers may also be formed using painting, screen printing, vacuum coating or sputtering techniques.

The substrate 104 itself is preferably formed of a polyester resin, such as that commercially available under the trade name Mylar ®, being on the order of 3 mils (0.076 mm) thick. The substrate may also be formed of Kapton ®, or other suitable material. The preferred length of the substrate section 104a is 23.75" (60 cm), with a distance of 3.75" (9.5 cm) between each precordial electrode site $V_1$-$V_6$. A suitable width for the substrate section 104a is 1.2" (3 cm), excluding end segment 110. A suitable length for the substrate sections 104b and 104e is 19.25" (49 cm). A suitable width for the substrate sections 104b–104e is on the order of 0.3" (7.6 mm).

Once the conductors 114 have been formed on the substrate 104, the oval-shaped layers 116 are deposited or otherwise placed onto the lower surface 124 of the substrate, with a different layer 116 being in electrical contact with each conductor 114. Although not depicted in FIG. 15, the precordial and limb sites may be ionically coupled to a person's skin through a conductive interface, such as the conductive gel pads 38 shown in FIGS. 10 and 11. The oval-shaped layers 116 provide better contact with a conductive interface such as the gel pads 38, as opposed to simply having the end of the conductors 114 contact the interface. The oval-shaped layers 116 may also be of other shapes, for example, circular or of various thicknesses. The oval-shaped layers 116 are preferably of a silver/silver chloride compound. The silver/silver chloride layer converts the ionic current flow of the body into electron flow that the monitor can amplify in a chemically reversible manner which is well known to those skilled in the art. The conductors 114 could be formed of silver/silver chloride but are generally formed of silver which is more conductive and does not represent a source of chloride ions which would corrode the connector. The silver by itself does not bidirectionally transform ionic flow to electron flow. After deposition of the oval-shaped layers 116, the cover layers 122 are deposited or otherwise formed on the conductors 114 to insulate the portions of the conductors between the end segment 110 and each oval-shaped layer 116.

After formation of the conductors 114, oval-shaped layers 116 and cover layer 122, a band 126 of malleable metal or other material is attached to the upper surface 128 of each substrate section 104a–104e, i.e., opposite the conductors 114 (only substrate section 104a is shown in FIG. 17). Each band 126 is somewhat narrower than the substrate section on which it is placed. The band attached to the substrate section 104a is significantly wider than the bands attached to substrate sections 104b–104e, although the bands have not been illustrated in FIG. 16 for purposes of clarity in the illustration. In an actual embodiment, the bands 126 are formed of a dead-soft aluminum on the order of 6 mils (0.15 mm) thick. Other malleable metals or plastics may also be used.

The bands 126 are attached, for example, by including a pressure-sensitive adhesive layer on one side thereof and firmly pressing the adhesive layer against the upper surface 128 of the electrode strip. The band 126 need not be a continuous band that extends the entire length of the substrate sections 104a–104e. Rather, it is useful in some applications to have sections of the band attached only to the areas upon which regions of extensibility are to be formed. Thus, for example, substrate section 104a would include five separate malleable bands, each separated by one of the electrode sites $V_1$–$V_6$.

The substrate 104, including the conductors 114, cover layers 122 and bands 126, is flexible but substantially inextendible along its length prior to formation of the regions of extensibility 102. The regions of extensibility 102 are formed into the substrate section 104a between pairs of adjacent precordial electrode sites $V_1$–$V_6$. Preferably, the regions of extensibility 102 are also formed into the substrate sections 104b–104e during the same process. However, it is noted that the regions of extensibility do not have to be formed into the substrate sections 104b–104e, but formation therein is often a manufacturing convenience. As will be appreciated, if regions of extensibility are not formed in the substrate sections 104b–104e, the band 126 may be omitted from these sections, if desired.

With reference again to FIG. 17, the electrode strip 100 preferably includes gel pads 38, similar to those depicted in FIG. 10, that are preattached to the area surrounding each electrode site. The gel pads 38 each have a lower surface 42 that provides ionic conductivity between the conductors 114 and a person's skin. An outer liner 44 protects the adhesive lower surface of the gel pads 38 and is removed just prior to attaching the strip to a body.

A preferred arrangement of the regions of extensibility 102 is shown in FIG. 16, wherein each region includes four transverse, upwardly extending folds 130 in the substrate/band assembly. In cross section, each fold 130 defines an inverted, U-shaped section of substrate. The bands 126 retain the initially formed four-fold configuration of each region of extensibility until acted upon during placement of the electrode strip. Upon adjusting the regions of extensibility during placement of the strip, the regions will retain the adjusted form (as a result of the bands 126), and thus the electrode sites will have a tendency to remain where they are positioned, even before coupling each site to the body. As will be appreciated, other configurations of the regions of extensibility 102 may be used. For example, fewer or additional transverse folds 130 may be induced into the substrate. Moreover, various shapes and sizes of folds may also be implemented to form the regions of extensibility 102.

The regions of extensibility 102 are formed into the electrode strip 100 through mechanical processes. One process involves (1) aligning the strip along the top of a toothed surface, (2) extending an arm downwardly between a pair of adjacent teeth, thereby forcing the electrode strip into the groove formed by the adjacent teeth and creating one of the transverse folds, (3) positioning the arm above the next pair of teeth, and (4) repeating steps (2) and (3) until each region of extensibility is formed. Other processes known and used for the general formation of malleable material may also be used to form the regions of extensibility 102.

The process of forming the regions of extensibility 102 can be compared to formation of the regions of extensibility 30 shown in FIGS. 4–6. Formation of the regions of extensibility 30 requires the step of (1) preshaping the electrode strip, (2) heating the strip while in the preshaped position, and (3) cooling the strip. In contrast, heating is not required in the formation of the regions of extensibility 102; a desired shape is mechanically induced into the electrode strip, wherein the shape is held by the malleable layer attached to the substrate. The latter process has manufacturing advantages including that it is generally quicker and does not require heating and cooling of the electrode strip.

As will be appreciated, formation of each fold 130 decreases the longitudinal length of the strip, bringing the precordial electrode sites on either side of the fold closer together. In the application of the electrode strip 100 to person 18, the longitudinal distance between the electrode sites can then be increased by deforming the regions of extensibility 102, i.e., stretching the folds 130. Further, the strip may be bent laterally at the regions of extensibility by holding one side of the strip and pulling the free end of the strip, on the opposite side, in the direction of the desired bend. Thus, the resultant regions of extensibility 102 allow extension and curvilinear motion between adjacent electrode sites on the otherwise inextendible substrate 104.

There are a number of differences between the electrode strip 100 of FIGS. 14–16 and the electrode strip 10 of FIG. 1. The most significant difference is with respect to the regions of extensibility that are formed in each strip. The regions of extensibility 30 in strip 10 are resilient and have a tendency to return back to their formed shape once longitudinal or curvilinear pressure is removed from the strip. In contrast, the regions of extensibility 102 in strip 100, as a result of the bands 126, tend to conform to and retain any shape induced upon them, for example, as the electrode strip 100 is manipulated to properly position the precordial and limb sites on the body of a person. In effect, each region of extensibility 102 has a memory-like feature that allows the strip 100 to be shaped prior to actually connecting the electrode sites to the person. This provides an opportunity for greater accuracy in electrode placement. Further, as is illustrated most clearly in FIG. 16, the multifolded structure of each region of extensibility 102 provides for an accordion-like bending of the regions of extensibility, whereby curves in the electrode strip are readily achieved along with the desired electrode site separations.

It is noted that the bands 126 may also act as a shielding layer to shield the conductors 114 from electromagnetic waves if the bands 126 are connected to ground. As is known in the art, highly sensitive medical instruments will typically have shielded cables to block at least a portion of the spurious currents induced by ambient electromagnetic waves. In a somewhat similar fashion, the bands 126 could shield the conductors 114 from electromagnetic interference, thereby enhancing the accuracy of the ECG readings. The amount of shielding provided by each band will generally depend upon the composition of the material used to form the band, the dimension thereof, and mainly where it is connected to the electrical ground reference.

FIG. 18 is a partial illustration of a third exemplary embodiment of an electrode strip in accordance with the invention. In the embodiment of FIG. 18, a variation of strip 100 is shown, including the substrate section 104a and band 126. However, the conductors 114, oval-shaped layers 116 and cover layers 122 are not manufactured as part of the strip. Rather, the conductors and cover layers are in effect replaced by a plurality of electrode pads 140 and separate and distinct cables 142 that carry electrical signals from the electrode pads 140 to therapeutic and monitoring equipment. Although a variation of the electrode strip 100 is depicted in FIG. 18 and described below, the method shown and described herein will work equally well with a variation of the electrode strip 10 of FIG. 1, i.e., one that does not include the conductors or cover layer but does include an electrode element electrically connected to a tabular region.

An alternative embodiment to that depicted in FIG. 18 would be an extendible substrate that did not require the use of a plurality of transverse folds 130. Examples of such a material might be Coban ® manufactured by 3M, a natural rubber, or an inelastic plastically deformable material such as thin polyethylene sheet.

Each electrode pad 140 has adhesive layers on oppositely disposed surfaces: an upper adhesive layer 144 to attach the electrode pad 140 to the electrode strip, and a lower conductive adhesive layer 146 to detachably mount the pad to the body of a person (not shown). The lower adhesive layer 146 is exposed by removing a protective liner 148. Each electrode pad 140 further includes a conductive tabular region 150 that projects from the pad. An alligator clip 152, coupled to the cable 142, is then used to provide an electrical connection to the cable. A conductive element within the electrode pad couples electrical signals from the lower adhesive layer 146 (i.e., which provides a conductive interface with the person's skin) to the tabular region 150.

In the embodiment of FIG. 18, the electrode sites are first positioned on the body of the person, and then each site is coupled to medical equipment through a different one of the cables 142. As will be appreciated, the conductive gel pads 38 of FIG. 11 may be used as an alternative to the electrode pads 140 if they are provided with a conductive tabular region to allow electrical connection between the pad and cables 142. Use of the adhesive electrode pads 140 and cables 142 is advantageous from a manufacturing standpoint in that the electrode strip does not need conductors or the dielectric cover layers. However, use of the pad/cable combination in lieu of the conductors is disadvantageous because care must be exercised to ensure that the right cable is connected to the corresponding electrode. Errors in the connection scheme can lead to incorrect computer analysis of the results.

FIGS. 19 and 20 illustrate an exemplary body surface potential mapping assembly 160 constructed in accordance with the present invention. As will be appreciated, any number of other body surface potential mapping patterns may also be realized.

The mapping assembly 160 includes 29 electrode sites provided on four separate electrode strips 162, 164, 166 and 168, each employing the basic constructional techniques described in connection with the electrode strip 100 of FIG. 14. Although not explicitly illustrated in FIGS. 19 and 20, each electrode strip preferably includes (a) a substrate, (b) a plurality of conductors that extend from a connector segment 170 of each electrode strip, along a lower surface of the substrate, to individual electrode sites, (c) a malleable band attached to an upper surface of the substrate, (d) a plurality of cover layers that extend over the conductors to insulate all but a portion of the conductors from the body of a person, (e) a silver/silver chloride layer over each electrode site, and (f) an adhesive layer positioned over each silver/silver chloride layer to attach the strip to a person. Other methods of constructing the electrode strips, such as those discussed above in regard to the electrode strip 10 of FIG. 1, may also be employed.

As is shown in FIG. 19, a number of clamps 120 cooperate with the connector segments 170 to releasably couple the conductors of each electrode strip to individual cables 172. The connector segments 170 are constructed similar to the end segment 110 of the electrode strip 100, shown in FIG. 15. The cables 172, in turn, couple the conductors to medical and therapeutic equipment (not shown) through a main cable connector 174 including four sets of receptacles and a main cable 176. The cables 172 each include a connector at the end thereof, opposite clamp 120. The connectors are releasably coupleable to the receptacles in the main cable connector 174, which has at least as many conductors as the four strips 162, 164, 166 and 168 combined. Each conductor in the main cable connector 174 is coupled to medical equipment through the cable 176, which also includes at least as many conductors as the number contained in the strips.

A plurality of regions of extensibility 102 are provided between at least some of the electrode sites on the strips to provide electrode site separation and strip curvature, thereby allowing the electrode sites to be properly positioned on the body of a person 18. The regions of extensibility 102 have in some instances been labeled with different reference numerals for clarity in the description of the electrode strips. With reference to FIG. 19, the electrode sites positioned on the person's sides are not shown because of the view presented. FIG. 20 is provided to better visualize the location of all of the 29 electrodes, particularly those not illustrated in FIG. 19. In FIG. 20 the electrode strips and electrode sites are illustrated on a plane superimposed on the body of a person 18. A pair of mid-lines 178 and 180, located along the right and left sides of the person 18, respectively, represent imaginary lines that would extend along the person's sides, separating the body into front and back portions, in the event the strips were applied to the person's body.

Reviewing each electrode strip in greater detail, electrode strip 162 includes left and right columns 162L and 162R of electrode sites 182a–182h that are coupled together at their respective upper and lower ends by regions of extensibility 184a and 184b, respectively. Each column includes four electrode sites. When strip 162 is properly applied to the person's chest, columns 162L and 162R are positioned on opposite sides of the person's sternum. It is noted that regions of extensibility are not included between the electrode sites within a column because the preferred locations and separations of these electrode sites along the sternum are generally the same for a large percentage of the population.

Electrode strip 164 is positioned on the left, mid-level chest area of the person and includes two rows 164a and 164b of electrode sites that are separable from one another at an end of the strip opposite the connector segment 170. The upper electrode strip 164a includes four electrode sites 186a–186d; the lower electrode strip 164b includes three electrode sites 186e–186g. With reference to FIG. 20, the electrode sites 186c and 186g (third from the connector segment 170) are positioned on the person's left side, in front of mid-line 180. The electrode site 186d, fourth from the connector segment 170, is also positioned on the person's left side, but behind mid-line 180.

The electrode strips 166 and 168 are positioned above and below, respectively, the electrode strips 162 and 164. The electrode strips 166 and 168 are identical, with strip 166 including seven electrode sites 188a–188g and strip 168 including sites 190a–190g. The fight outermost electrode sites, 188a and 190a, are positioned on the person's right side, behind mid-line 178. The electrode sites adjacent the right outermost electrode sites, 188b and 190b, are positioned on the person's fight side, in front of mid-line 178. The left outermost electrode sites, 188g and 190g, are positioned on the person's left side, behind mid-line 180. The electrodes adjacent the left outermost electrode sites, 188f and 190f, are positioned on the person's left side, in front of mid-line 180.

The remaining electrode sites on the top electrode strip 166 are positioned across the chest area of the person, one on the person's right, 188c, and two on the left 188c and 188d. The remaining electrode sites on the bottom electrode strip 168 are positioned across the abdominal area, with electrode site 190c being on the fight side and electrode sites 190d and 190e being on the person's left side.

The electrode assembly 160 utilizes the technology described in the present invention to provide a 29 electrode site body surface potential mapping scheme. It will be appreciated by those skilled in the art that virtually any number of electrode sites may be implemented using this technology. Moreover, various other conductor-electrode site arrangements may be employed in accordance with the present invention.

Figure 21:
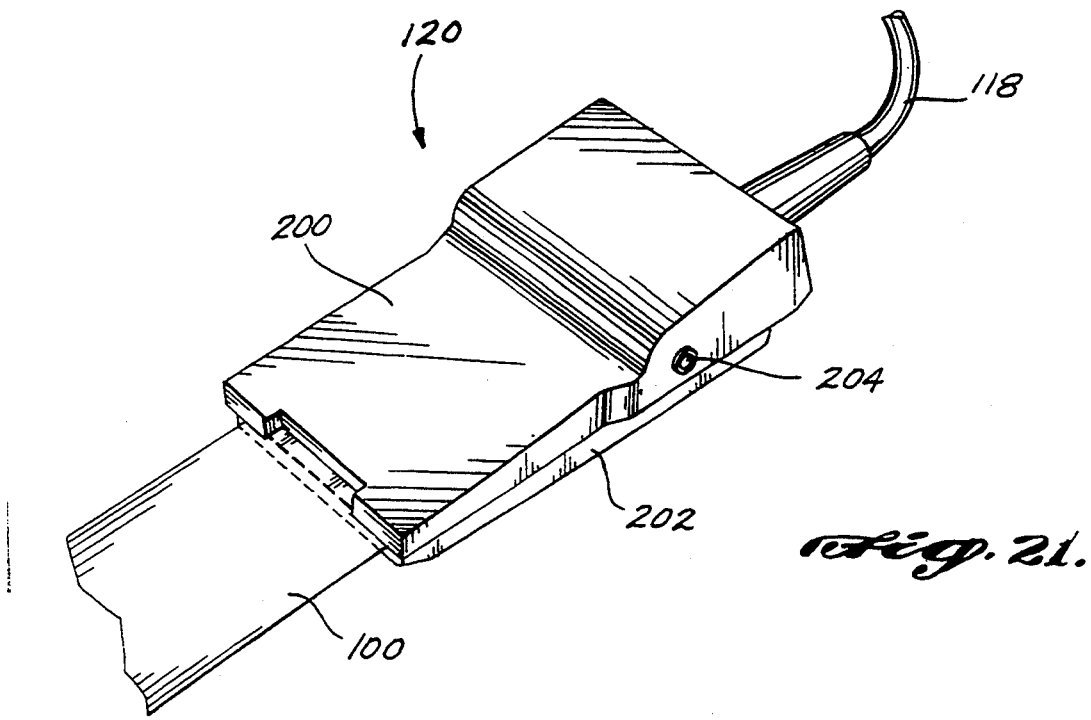
FIG. 21 is a perspective view of a connector used to couple the electrode strip to medical and diagnostic equipment.
Figure 22:
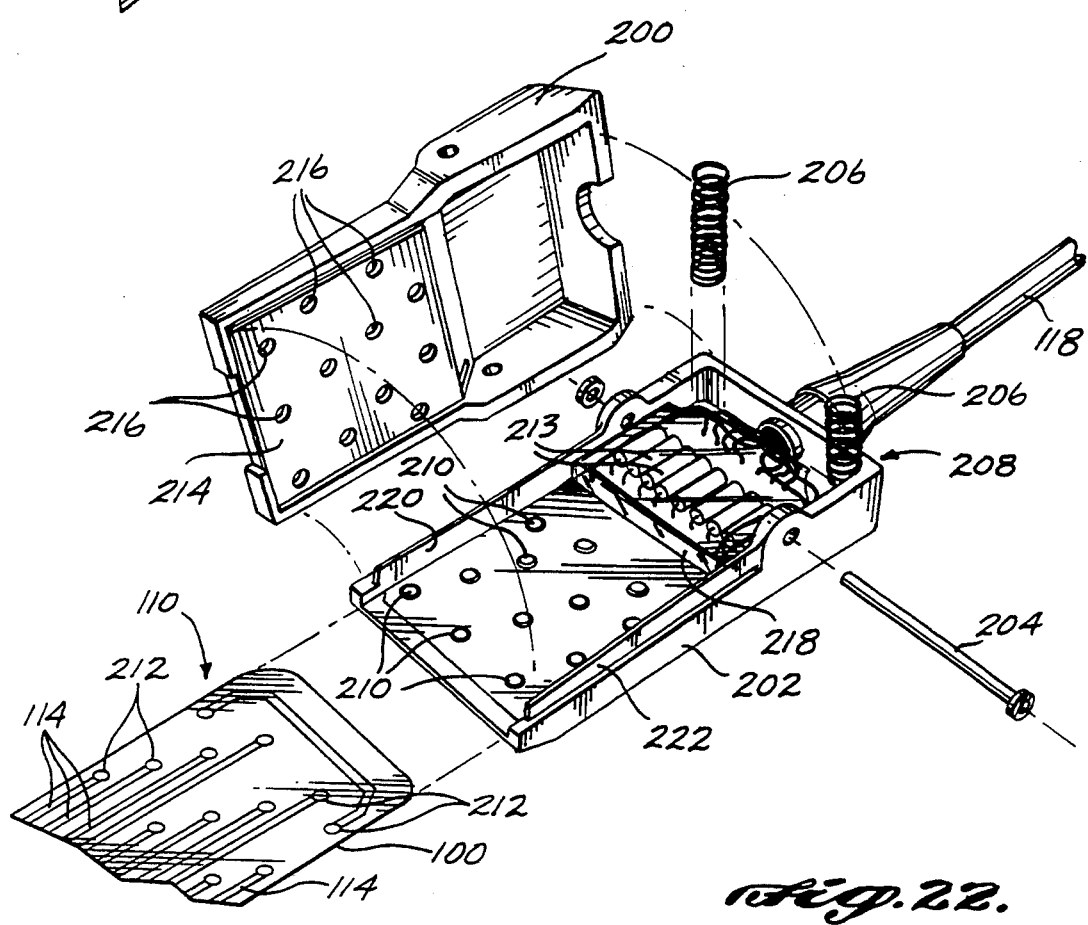
FIG. 22 is an exploded perspective view of the connector of FIG. 21.

FIGS. 21 and 22 illustrate in greater detail the clamp 120 used to connect the electrode strip 100 of FIGS. 14–17 to medical and diagnostic equipment (not shown) through cable 118. A similar clamp configuration would be used to couple the electrode strips of FIGS. 19 and 20 to medical and diagnostic equipment. Clamp 120 includes an upper and lower housing 200 and 202, respectively, that are coupled together by a pin 204. A pair of springs 206 are captured between the upper and lower housing near a back side 208 of the clamp. The lower housing 202 includes a plurality of conductive teeth 210 that are located in a pattern such that they intersect the terminating ends 212 of the conductors 114, when the electrode strip 100 is positioned within the clamp 120. As is shown, each terminating end 212 includes a circular conductive region that is slightly larger than the surface area of the conductive teeth 210. The arrangement of the conductive teeth 210 is based on the configuration of the terminating ends of the electrode strip.

In the embodiment of FIGS. 21 and 22, twelve conductive teeth are included in the lower housing 202, ten of which correspond to the conductors 114a–114j of FIG. 15, and two that may be connected to ground or used for other purposes. For example, additional conductive teeth may be used to determine whether the electrode strip has been inserted into the connector properly or whether the appropriate connector/electrode strip pairing has been implemented. Each of the conductive teeth 210 are coupled to a separate conductor within the cable 118. A plurality of resistors 213 may be coupled between at least some of the conductive teeth and cable 118. The resistors 213 are used to limit defibrillation current through the cable and monitor. In the embodiment of FIG. 22, nine resistors 213 are depicted, although one of the resistors is partially hidden by the lower housing 202.

The upper housing 200 includes a pad 214 having a plurality of apertures 216 extending therethrough. The apertures 216 are positioned directly above the conductive teeth 210 when the upper housing is seated on the lower housing such that the pad 214 abuts the electrode strip 100, which in turn is pressed against the conductive teeth 210. Apertures allow elastic deformation of the compliant electrode strip connector end segment 110 between the conductive teeth 210 and the aperture perimeter which is also resiliently deformable. This secondary spring action helps assure electrical contact without the added manufacturing expense of spring loaded contacts and or tighter tolerances.

To releasably connect the clamp 120 to the electrode strip 100, the upper and lower housings are pressed together at the back 208 of the clamp, causing the upper housing 200 to rotate, relative to the lower housing 202, around the pin 204. Rotation of the upper housing 200 provides an opening for insertion of the end segment 110 of the electrode strip 100 into the clamp. The lower housing 202 includes a back wall 218 that prevents the end segment 110 from being inserted too fax into the clamp 120, and left and right side walls 220 and 222 that ensure the electrode strip is properly seated as it is positioned into the clamp. After the end segment has been inserted, pressure is released from the back 218 of the clamp. The springs 206 cause the upper housing 200 to rotate about the pin 204, pressuring the pad 214 into abutment with the electrode strip 100 and the terminating ends 212 of the conductors 114 against the conductive teeth 210, thereby making electrical contact.

A suitable material for constructing the upper and lower housings is a plastic that has been molded into the depicted shapes. The pad is preferably comprised of a compliant material such as silicone rubber. The conductive teeth are preferably noble metal plated electrical contacts.

It should be recognized by those skilled in the art that various modifications and changes can be made in the disclosed embodiments of the invention without departing from the spirit and scope of the invention. Therefore, the scope of the invention should be determined solely by reference to the following claims.

The embodiments of the invention in which an exclusive property or privilege is claimed are defined as follows:

1. An electrode strip for placement on a body, comprising:
   a substantially inextendible substrate having a plurality of electrode sites defined on the substrate and a region of extensibility defined in the substrate between a pair of adjacent electrode sites; and
   conductive means for providing an electrical path to each electrode site.

2. The electrode strip of claim 1, and further including a layer of malleable material attached to the substrate.

3. The electrode strip of claim 1, wherein the conductive means includes a plurality of spaced-apart conductors that extend to a different one of the electrode sites.

4. The electrode strip of claim 3, and further including means for coupling the conductors to the body.

5. The electrode strip of claim 4, wherein the means for coupling comprises a plurality of adhesive conductive gel pads, each of the gel pads coupling a different one of the conductors to the body.

6. The electrode strip of claim 5, wherein each conductive gel pad includes an upper surface, only a portion of which is attached to the substrate to allow the substrate to bend away from the conductive gel pad.

7. The electrode strip of claim 3, and further including a plurality of dielectric cover layers, a different one of the cover layers extending over each conductor.

8. The electrode strip of claim 3, and further including an insulating cover layer that extends over the conductors, the cover layer including a plurality of apertures extending therethrough and being positioned so that a conductor extends at least partially across each one of the apertures to form the electrode sites.

9. The electrode strip of claim 3, wherein the substrate is elongate and the conductors extend longitudinally from a first end of the substrate to each electrode site.

10. The electrode strip of claim 1, wherein each region of extensibility includes a plurality of transverse folds in the substrate.

11. The electrode strip of claim 10, wherein a cross section of each fold defines a substantially U-shaped section in the substrate.

12. The electrode strip of claim 1, wherein the electrode strip is for use with medical equipment and wherein the conductive means includes:
a plurality of electrode pads, each pad including a tabular region, with a separate pad being coupled to each electrode site; and
a plurality of separate and distinct lead wires coupleable to the medical equipment and including means for coupling the lead wires to the tabular regions of the electrode pads.

13. An electrode strip for placement on a body, comprising:
a substrate having a plurality of electrode sites defined on the substrate;
conductive means for providing an electrical path to each electrode site; and
a layer of malleable material attached to the substrate, the substrate and malleable material having a region of extensibility defined therein between a pair of adjacent electrode sites to allow selective positioning of the adjacent electrode sites on the body.

14. The electrode strip of claim 13, wherein each region of extensibility includes a plurality of transverse folds in the substrate.

15. The electrode strip of claim 14, wherein a cross section of each fold defines a U-shaped section in the electrode strip.

16. The electrode strip of claim 13, wherein the conductive means includes a plurality of spaced-apart conductors that extend along the substrate to a different one of the electrode sites.

17. The electrode strip of claim 16, and further including a plurality of dielectric cover layers, a different one of the cover layers extending over each conductor.

18. The electrode strip of claim 16, and further including an insulating cover layer that extends over the conductors, the cover layer including a plurality of apertures extending therethrough and being positioned so that a conductor extends at least partially across each one of the apertures to form the electrode sites.

19. An assembly of electrodes for placement on a body, comprising:
first and second electrode strips, each strip comprising a substrate having a plurality of electrode sites defined on the substrate, a region of extensibility defined in the substrate between a pair of adjacent electrode sites, and conductive means for providing an electrical path to the electrode sites of each electrode strip; and
means for connecting the electrode strips.

20. The assembly of claim 19, wherein each electrode strip further includes a layer of malleable material attached to the substrate of the electrode strip.

21. The assembly of claim 19, wherein the regions of extensibility of at least one of the substrates includes a plurality of transverse folds in the substrate.

22. The assembly of claim 21, wherein the folds, in cross section, resemble a U-shape.

23. The assembly of claim 19, wherein each electrode strip includes a plurality of spaced-apart conductors that extend along the substrate of each electrode strip to a different one of the electrode sites on the electrode strip.

24. The assembly of claim 23, wherein the electrode strips further include a plurality of dielectric cover layers, with a different one of the cover layers extending over each conductor.

25. The assembly of claim 23, wherein each electrode strip further includes an insulating cover layer that extends over the conductors, the cover layer including a plurality of apertures extending therethrough and being positioned so that a conductor extends at least partially across one of the apertures to form the electrode sites.

26. An electrode strip having a plurality of electrode sites, the electrode strip for placement on a body by a user, comprising:
(a) a substrate including a connector segment and upper and lower surfaces;
(b) a plurality of conductors, each conductor extending from the connector segment of the substrate, along the lower surface to an electrode site;
(c) means for insulating the conductors;
(d) a layer of malleable material attached to the upper surface of the substrate; and
(e) means, defined in the layer of malleable material, for allowing the longitudinal distance between pairs of adjacent electrode sites to be adjusted through manipulation of the strip by the user.

27. The electrode strip of claim 26, wherein the electrode strip includes six precordial electrode sites and four limb electrode sites.

28. The electrode strip of claim 26, including means for coupling the conductors to the body.

29. The electrode strip of claim 28, wherein the means for coupling includes a plurality of adhesive conductive gel pads, each of the gel pads coupling a different one of the conductors to the body.

30. The electrode strip of claim 26, wherein the means for insulating includes a plurality of dielectric cover layers, a different one of the cover layers extending over each conductor.

31. The electrode strip of claim 26, wherein the means for insulating includes an insulating cover layer that extends over the conductors, the cover layer including a plurality of apertures extending therethrough and being positioned so that a conductor extends at least partially across each one of the apertures to form the electrode sites.

32. The electrode strip of claim 26, wherein the means for adjusting the longitudinal distance between pairs of adjacent electrode sites includes a plurality of transverse folds in the substrate.

33. The electrode strip of claim 32, wherein a cross section of each fold defines a U-shaped section in the malleable material.

* * * * *

UNITED STATES PATENT AND TRADEMARK OFFICE
CERTIFICATE OF CORRECTION

PATENT NO. : 5,341,806
DATED : August 30, 1994
INVENTOR(S) : Gadsby et al.

It is certified that error appears in the above-indentified patent and that said Letters Patent is hereby corrected as shown below:

| COLUMN | LINE | ERROR |
|---|---|---|
| [57] Abstract | 6 | "layer(122)" should read --layer (122)-- |
| 16 | 9 | "(f)an" should read --(f) an-- |
| 17 | 14 | "fight" should read --right-- |
| 17 | 18 | "fight" should read --right-- |
| 17 | 30 | "fight" should read --right-- |
| 18 | 30 | "fax" should read --far-- |

Signed and Sealed this

Twenty-seventh Day of December, 1994

Attest:

BRUCE LEHMAN

*Attesting Officer*     *Commissioner of Patents and Trademarks*